(12) United States Patent
Watson

(10) Patent No.: US 8,083,789 B2
(45) Date of Patent: Dec. 27, 2011

(54) SECUREMENT ASSEMBLY AND METHOD FOR EXPANDABLE ENDOVASCULAR DEVICE

(75) Inventor: James R. Watson, Santa Rosa, CA (US)

(73) Assignee: Trivascular, Inc., Santa Rosa, CA (US)

( * ) Notice: Subject to any disclaimer, the term of this patent is extended or adjusted under 35 U.S.C. 154(b) by 245 days.

(21) Appl. No.: 11/941,450

(22) Filed: Nov. 16, 2007

(65) Prior Publication Data

US 2009/0132020 A1 May 21, 2009

(51) Int. Cl.
*A61F 2/06* (2006.01)
(52) U.S. Cl. ...................................... 623/1.12
(58) Field of Classification Search .................. None
See application file for complete search history.

(56) References Cited

U.S. PATENT DOCUMENTS

| | | |
|---|---|---|
| 3,076,737 A | 2/1963 | Roberts |
| 3,540,431 A | 11/1970 | Uddin |
| 3,631,854 A | 1/1972 | Fryer et al. |
| 3,657,744 A | 4/1972 | Ersek |
| 3,669,586 A | 6/1972 | Kramer |
| 3,814,137 A | 6/1974 | Martinez |
| 3,818,511 A | 6/1974 | Goldberg et al. |
| 3,902,198 A | 9/1975 | Cooper |
| 3,991,767 A | 11/1976 | Miller et al. |
| 4,096,227 A | 6/1978 | Gore |
| 4,110,392 A | 8/1978 | Yamasaki |
| 4,140,126 A | 2/1979 | Choudhury |
| 4,183,102 A | 1/1980 | Guiset |
| 4,187,390 A | 2/1980 | Gore |
| 4,208,745 A | 6/1980 | Okita |
| 4,214,587 A | 7/1980 | Sakura, Jr. |
| 4,229,838 A | 10/1980 | Mano |
| 4,248,924 A | 2/1981 | Okita |
| 4,385,093 A | 5/1983 | Hubis |
| 4,416,028 A | 11/1983 | Eriksson et al. |

(Continued)

FOREIGN PATENT DOCUMENTS

EP 0646365 4/1995

(Continued)

OTHER PUBLICATIONS

The AneuRx® Stent Graft System Treatment for AAA brochure, "An Innovative Modular Approach for the Treatment of Abdominal Aortic Aneurysms (AAA)," Medtronic AVE, INC. 1999.

(Continued)

*Primary Examiner* — Gary Jackson
*Assistant Examiner* — Kevin Everage
(74) *Attorney, Agent, or Firm* — Grant Anderson LLP

(57) ABSTRACT

A securement assembly for releasably securing an expandable stent or stent-graft relative to a delivery tube. The securement assembly comprises a belt base configured for securement relative to the delivery tube. The belt base defines a release member passage and a receiving portion. A first end of a belt is fixed relative to the belt base. The opposite end of the belt includes a retainment portion configured to releasably engage the receiving portion of the belt base. A release member is removably positioned through the release member passage and aligned with the belt retainment portion such that the retainment portion is maintained engaged with the receiving portion until the release member is moved to a non-aligned position. A method of releasably securing a portion of an expandable stent or stent-graft relative to a delivery tube is also provided.

8 Claims, 9 Drawing Sheets

U.S. PATENT DOCUMENTS

| | | | |
|---|---|---|---|
| 4,434,797 A | 3/1984 | Silander | |
| 4,459,252 A | 7/1984 | MacGregor | |
| 4,474,630 A | 10/1984 | Planck et al. | |
| 4,478,665 A | 10/1984 | Hubis | |
| 4,482,516 A | 11/1984 | Bowman et al. | |
| 4,497,074 A | 2/1985 | Rey et al. | |
| 4,503,569 A | 3/1985 | Dotter | |
| 4,512,338 A | 4/1985 | Balko et al. | |
| 4,550,447 A | 11/1985 | Seiler, Jr. et al. | |
| 4,552,707 A | 11/1985 | How | |
| 4,562,596 A | 1/1986 | Kornberg | |
| 4,577,631 A | 3/1986 | Kreamer | |
| 4,580,568 A | 4/1986 | Gianturco | |
| 4,592,754 A | 6/1986 | Gupte et al. | |
| 4,617,932 A | 10/1986 | Kornberg | |
| 4,647,416 A | 3/1987 | Seiler, Jr. et al. | |
| 4,655,769 A | 4/1987 | Zachariades | |
| 4,655,771 A | 4/1987 | Wallsten | |
| 4,665,906 A | 5/1987 | Jervis | |
| 4,705,517 A | 11/1987 | DiPisa, Jr. | |
| 4,731,073 A | 3/1988 | Robinson | |
| 4,733,665 A | 3/1988 | Palmaz | |
| 4,739,762 A | 4/1988 | Palmaz | |
| 4,740,207 A | 4/1988 | Kreamer | |
| 4,743,480 A | 5/1988 | Campbell et al. | |
| 4,760,102 A | 7/1988 | Moriyama et al. | |
| 4,776,337 A | 10/1988 | Palmaz | |
| 4,787,899 A | 11/1988 | Lazarus | |
| 4,816,028 A | 3/1989 | Kapadia et al. | |
| 4,830,003 A | 5/1989 | Wolff et al. | |
| 4,856,516 A | 8/1989 | Hillstead | |
| 4,871,365 A | 10/1989 | Dumican | |
| 4,877,661 A | 10/1989 | House et al. | |
| 4,902,423 A | 2/1990 | Bacino | |
| 4,932,938 A | 6/1990 | Goldberg et al. | |
| 4,941,870 A | 7/1990 | Okada et al. | |
| 4,955,899 A | 9/1990 | Della et al. | |
| 4,957,669 A | 9/1990 | Primm | |
| 4,985,296 A | 1/1991 | Mortimer, Jr. | |
| 4,994,071 A | 2/1991 | MacGregor | |
| 4,994,077 A | 2/1991 | Dobben | |
| 5,019,090 A | 5/1991 | Pinchuk | |
| 5,041,126 A | 8/1991 | Gianturco | |
| 5,052,998 A | 10/1991 | Zimmon | |
| 5,059,211 A | 10/1991 | Stack et al. | |
| 5,064,435 A | 11/1991 | Porter | |
| 5,098,625 A | 3/1992 | Huang et al. | |
| 5,100,422 A | 3/1992 | Berguer et al. | |
| 5,104,399 A | 4/1992 | Lazarus | |
| 5,104,400 A | 4/1992 | Berguer et al. | |
| 5,104,404 A | 4/1992 | Wolff | |
| 5,108,424 A | 4/1992 | Hoffman, Jr. et al. | |
| 5,110,527 A | 5/1992 | Harada et al. | |
| 5,116,365 A | 5/1992 | Hillstead | |
| 5,122,154 A | 6/1992 | Rhodes | |
| 5,123,917 A | 6/1992 | Lee | |
| 5,133,732 A | 7/1992 | Wiktor | |
| 5,135,536 A | 8/1992 | Hillstead | |
| 5,139,480 A | 8/1992 | Hickle et al. | |
| 5,150,304 A | 9/1992 | Berchem et al. | |
| 5,151,105 A | 9/1992 | Kwan-Gett | |
| 5,152,782 A | 10/1992 | Kowligi et al. | |
| 5,156,620 A | 10/1992 | Pigott | |
| 5,163,955 A | 11/1992 | Love | |
| 5,167,614 A | 12/1992 | Tessmann | |
| 5,171,262 A | 12/1992 | MacGregor | |
| 5,192,310 A | 3/1993 | Herweck et al. | |
| 5,195,984 A | 3/1993 | Schatz | |
| 5,197,976 A | 3/1993 | Herweck et al. | |
| 5,197,978 A | 3/1993 | Hess | |
| 5,201,757 A | 4/1993 | Heyn et al. | |
| 5,202,352 A | 4/1993 | Okada et al. | |
| 5,207,695 A | 5/1993 | Trout, III | |
| 5,217,483 A | 6/1993 | Tower | |
| 5,219,355 A | 6/1993 | Parodi et al. | |
| 5,226,913 A | 7/1993 | Pinchuk | |
| 5,234,456 A | 8/1993 | Silvestini | |
| 5,250,059 A | 10/1993 | Andreas et al. | |
| 5,275,622 A | 1/1994 | Lazarus et al. | |
| 5,282,823 A | 2/1994 | Schwartz et al. | |
| 5,282,824 A | 2/1994 | Gianturco | |
| 5,282,847 A | 2/1994 | Trescony et al. | |
| 5,290,305 A | 3/1994 | Inoue | |
| 5,292,331 A | 3/1994 | Boneau | |
| 5,304,200 A | 4/1994 | Spaulding | |
| 5,314,472 A | 5/1994 | Fontaine | |
| 5,316,023 A | 5/1994 | Palmaz et al. | |
| 5,320,100 A | 6/1994 | Herweck et al. | |
| 5,321,109 A | 6/1994 | Bosse et al. | |
| 5,330,528 A | 7/1994 | Lazim | |
| 5,334,164 A | 8/1994 | Guy et al. | |
| 5,334,201 A | 8/1994 | Cowan | |
| 5,344,426 A | 9/1994 | Lau et al. | |
| 5,344,444 A | 9/1994 | Glastra | |
| 5,344,451 A | 9/1994 | Dayton | |
| 5,350,398 A | 9/1994 | Pavcnik | |
| 5,354,310 A | 10/1994 | Garnic et al. | |
| 5,354,329 A | 10/1994 | Whalen | |
| 5,360,443 A | 11/1994 | Barone et al. | |
| 5,365,996 A | 11/1994 | Crook | |
| 5,366,504 A | 11/1994 | Andersen et al. | |
| 5,370,682 A | 12/1994 | Schmitt | |
| 5,370,691 A | 12/1994 | Samson | |
| 5,374,473 A | 12/1994 | Knox et al. | |
| 5,382,261 A | 1/1995 | Palmaz | |
| 5,383,892 A | 1/1995 | Cardon et al. | |
| 5,383,928 A | 1/1995 | Scott et al. | |
| 5,387,235 A | 2/1995 | Chuter et al. | |
| 5,389,106 A | 2/1995 | Tower et al. | |
| 5,391,147 A | 2/1995 | Imran et al. | |
| 5,397,345 A | 3/1995 | Lazarus | |
| 5,405,377 A | 4/1995 | Cragg | |
| 5,405,378 A | 4/1995 | Strecker | |
| 5,405,379 A | 4/1995 | Lane | |
| 5,411,550 A | 5/1995 | Herweck et al. | |
| 5,415,634 A | 5/1995 | Glynn et al. | |
| 5,423,851 A | 6/1995 | Samuels | |
| 5,433,909 A | 7/1995 | Martakos et al. | |
| 5,437,900 A | 8/1995 | Kuzowski | |
| 5,441,515 A | 8/1995 | Khosravi et al. | |
| 5,443,458 A | 8/1995 | Eury | |
| 5,443,498 A | 8/1995 | Fountaine | |
| 5,445,646 A | 8/1995 | Euteneuer et al. | |
| 5,447,152 A | 9/1995 | Kohsai et al. | |
| 5,449,373 A | 9/1995 | Pinchasik et al. | |
| 5,456,713 A | 10/1995 | Chuter | |
| 5,464,419 A | 11/1995 | Glastra | |
| 5,464,449 A | 11/1995 | Ryan et al. | |
| 5,466,509 A | 11/1995 | Kowligi et al. | |
| 5,474,824 A | 12/1995 | Martakos et al. | |
| 5,476,506 A | 12/1995 | Lunn | |
| 5,476,589 A | 12/1995 | Bacino | |
| 5,478,330 A | 12/1995 | Imran et al. | |
| 5,480,423 A | 1/1996 | Ravenscroft et al. | |
| 5,489,295 A | 2/1996 | Piplani et al. | |
| 5,505,887 A | 4/1996 | Zdrahala et al. | |
| 5,507,769 A | 4/1996 | Marin et al. | |
| 5,507,770 A | 4/1996 | Turk | |
| 5,512,360 A | 4/1996 | King | |
| 5,514,154 A | 5/1996 | Lau et al. | |
| 5,522,880 A | 6/1996 | Barone et al. | |
| 5,522,881 A | 6/1996 | Lentz | |
| 5,522,883 A | 6/1996 | Slater et al. | |
| 5,524,633 A | 6/1996 | Heaven et al. | |
| 5,527,353 A | 6/1996 | Schmitt | |
| 5,527,355 A | 6/1996 | Ahn | |
| 5,529,653 A | 6/1996 | Glastra | |
| 5,529,820 A | 6/1996 | Nomi et al. | |
| 5,534,024 A | 7/1996 | Rogers et al. | |
| 5,536,274 A | 7/1996 | Neuss | |
| 5,545,135 A | 8/1996 | Iacob et al. | |
| 5,549,662 A | 8/1996 | Fordenbacher | |
| 5,549,663 A | 8/1996 | Cottone, Jr. | |
| 5,552,100 A | 9/1996 | Shannon et al. | |
| 5,554,180 A | 9/1996 | Turk | |
| 5,554,181 A | 9/1996 | Das | |
| 5,554,183 A | 9/1996 | Nazari | |

| | | | | | |
|---|---|---|---|---|---|
| 5,554,185 A | 9/1996 | Block et al. | 5,723,004 A | 3/1998 | Dereume et al. |
| 5,556,414 A | 9/1996 | Turi | 5,725,547 A | 3/1998 | Chuter |
| 5,556,426 A | 9/1996 | Popadiuk et al. | 5,725,549 A | 3/1998 | Lam |
| 5,560,986 A | 10/1996 | Mortimer, Jr. | 5,728,131 A | 3/1998 | Frantzen et al. |
| 5,562,697 A | 10/1996 | Christiansen | 5,733,303 A | 3/1998 | Israel et al. |
| 5,562,724 A | 10/1996 | Vorwerk et al. | 5,733,325 A | 3/1998 | Robinson et al. |
| 5,562,726 A | 10/1996 | Chuter | 5,735,892 A | 4/1998 | Myers et al. |
| 5,562,727 A | 10/1996 | Turk et al. | 5,735,893 A | 4/1998 | Lau et al. |
| 5,562,728 A | 10/1996 | Lazarus et al. | 5,735,897 A | 4/1998 | Buirge |
| 5,569,295 A | 10/1996 | Lam | 5,741,324 A | 4/1998 | Glastra |
| 5,571,171 A | 11/1996 | Barone et al. | 5,741,325 A | 4/1998 | Chaikof et al. |
| 5,571,172 A | 11/1996 | Chin | 5,747,128 A | 5/1998 | Campbell et al. |
| 5,571,173 A | 11/1996 | Parodi | 5,749,880 A | 5/1998 | Banas et al. |
| 5,575,817 A | 11/1996 | Martin | 5,749,894 A | 5/1998 | Engelson |
| 5,575,818 A | 11/1996 | Pinchuk | 5,749,920 A | 5/1998 | Quiachon et al. |
| 5,578,071 A | 11/1996 | Parodi | 5,749,921 A | 5/1998 | Lenker et al. |
| 5,578,072 A | 11/1996 | Barone et al. | 5,755,772 A | 5/1998 | Evans et al. |
| 5,588,964 A | 12/1996 | Imran et al. | 5,755,776 A | 5/1998 | Al-Saadon |
| 5,591,195 A | 1/1997 | Taheri et al. | 5,766,203 A | 6/1998 | Imran et al. |
| 5,591,197 A | 1/1997 | Orth et al. | 5,769,882 A | 6/1998 | Fogarty et al. |
| 5,591,229 A | 1/1997 | Parodi | 5,769,885 A | 6/1998 | Quiachon et al. |
| 5,597,378 A | 1/1997 | Jervis | 5,769,887 A | 6/1998 | Brown et al. |
| 5,603,721 A | 2/1997 | Lau et al. | 5,772,884 A | 6/1998 | Tanaka et al. |
| 5,607,478 A | 3/1997 | Lentz et al. | 5,776,142 A | 7/1998 | Gunderson |
| 5,609,624 A | 3/1997 | Kalis | 5,776,161 A | 7/1998 | Globerman |
| 5,609,625 A | 3/1997 | Piplani et al. | 5,776,183 A | 7/1998 | Kanesaka et al. |
| 5,609,627 A | 3/1997 | Goicoechea et al. | 5,780,807 A | 7/1998 | Saunders |
| 5,609,628 A | 3/1997 | Keranen | 5,782,789 A | 7/1998 | Herweck et al. |
| 5,609,629 A | 3/1997 | Fearnot | 5,782,838 A | 7/1998 | Beyar et al. |
| 5,612,885 A | 3/1997 | Love | 5,782,904 A | 7/1998 | White et al. |
| 5,618,301 A | 4/1997 | Hauenstein et al. | 5,782,909 A | 7/1998 | Quiachon et al. |
| 5,620,763 A | 4/1997 | House et al. | 5,785,679 A | 7/1998 | Abolfathi et al. |
| 5,626,599 A | 5/1997 | Bourne et al. | 5,788,626 A | 8/1998 | Thompson |
| 5,628,783 A | 5/1997 | Quiachon et al. | 5,789,047 A | 8/1998 | Sasaki et al. |
| 5,628,786 A | 5/1997 | Banas et al. | 5,797,951 A | 8/1998 | Mueller |
| 5,628,788 A | 5/1997 | Pinchuk | 5,798,924 A | 8/1998 | Eufinger et al. |
| 5,630,829 A | 5/1997 | Lauterjung | 5,799,384 A | 9/1998 | Schwartz et al. |
| 5,632,772 A | 5/1997 | Alcime et al. | 5,800,508 A | 9/1998 | Goicoechea et al. |
| 5,632,840 A | 5/1997 | Campbell | 5,800,512 A | 9/1998 | Lentz et al. |
| 5,639,278 A | 6/1997 | Dereume et al. | 5,800,515 A | 9/1998 | Nadal et al. |
| 5,641,373 A | 6/1997 | Shannon et al. | 5,800,518 A | 9/1998 | Piplani et al. |
| 5,645,915 A | 7/1997 | Kranzler et al. | 5,800,522 A | 9/1998 | Campbell et al. |
| 5,649,978 A | 7/1997 | Samson | 5,800,524 A | 9/1998 | Borghi |
| 5,653,745 A | 8/1997 | Trescony et al. | 5,800,526 A | 9/1998 | Anderson et al. |
| 5,653,746 A | 8/1997 | Schmitt | 5,810,870 A | 9/1998 | Meyers et al. |
| 5,656,029 A | 8/1997 | Imran et al. | 5,810,872 A | 9/1998 | Kanesaka et al. |
| 5,662,675 A | 9/1997 | Stockert et al. | 5,814,405 A | 9/1998 | Branca et al. |
| 5,662,700 A | 9/1997 | Lazarus | 5,817,102 A | 10/1998 | Johnson et al. |
| 5,665,115 A | 9/1997 | Cragg | 5,824,037 A | 10/1998 | Fogarty et al. |
| 5,665,117 A | 9/1997 | Rhodes | 5,824,039 A | 10/1998 | Piplani et al. |
| 5,667,523 A | 9/1997 | Bynon et al. | 5,824,041 A | 10/1998 | Lenker et al. |
| 5,669,936 A | 9/1997 | Lazarus | 5,824,042 A | 10/1998 | Lombardi et al. |
| 5,676,671 A | 10/1997 | Inoue | 5,824,044 A | 10/1998 | Quiachon et al. |
| 5,676,696 A | 10/1997 | Marcade | 5,824,046 A | 10/1998 | Smith et al. |
| 5,676,697 A | 10/1997 | McDonald | 5,824,058 A | 10/1998 | Ravenscroft et al. |
| 5,681,346 A | 10/1997 | Orth et al. | 5,827,289 A | 10/1998 | Reiley et al. |
| 5,683,449 A | 11/1997 | Marcade | 5,827,310 A | 10/1998 | Marin et al. |
| 5,683,451 A | 11/1997 | Lenker et al. | 5,827,320 A | 10/1998 | Richter et al. |
| 5,683,453 A | 11/1997 | Palmaz | 5,827,321 A | 10/1998 | Roubin et al. |
| 5,690,644 A | 11/1997 | Yurek et al. | 5,833,651 A | 11/1998 | Donovan et al. |
| 5,693,083 A | 12/1997 | Baker et al. | 5,833,707 A | 11/1998 | Mcintyre et al. |
| 5,693,084 A | 12/1997 | Chuter | 5,836,964 A | 11/1998 | Richter et al. |
| 5,693,087 A | 12/1997 | Parodi | 5,836,966 A | 11/1998 | St. Germain |
| 5,693,088 A | 12/1997 | Lazarus | 5,840,775 A | 11/1998 | Howard, Jr. et al. |
| 5,697,968 A | 12/1997 | Rogers et al. | 5,843,158 A | 12/1998 | Lenker et al. |
| 5,697,971 A | 12/1997 | Fischell et al. | 5,843,160 A | 12/1998 | Rhodes |
| 5,700,285 A | 12/1997 | Myers et al. | 5,843,162 A | 12/1998 | Inoue |
| 5,707,378 A | 1/1998 | Ahn et al. | 5,843,164 A | 12/1998 | Frantzen et al. |
| 5,707,388 A | 1/1998 | Lauterjung | 5,843,166 A | 12/1998 | Lentz et al. |
| 5,708,044 A | 1/1998 | Branca | 5,843,167 A | 12/1998 | Dwyer et al. |
| 5,709,701 A | 1/1998 | Parodi | 5,843,170 A | 12/1998 | Ahn |
| 5,709,703 A | 1/1998 | Lukie et al. | 5,843,173 A | 12/1998 | Shannon et al. |
| 5,712,315 A | 1/1998 | Dolan | 5,843,175 A | 12/1998 | Frantzen |
| 5,713,917 A | 2/1998 | Leonhardt et al. | 5,853,419 A | 12/1998 | Imran |
| 5,716,393 A | 2/1998 | Lindenberg et al. | 5,855,598 A | 1/1999 | Pinchuk |
| 5,716,395 A | 2/1998 | Myers et al. | 5,858,556 A | 1/1999 | Eckert et al. |
| 5,718,159 A | 2/1998 | Thompson | 5,861,027 A | 1/1999 | Trapp |
| 5,718,973 A | 2/1998 | Lewis et al. | 5,871,536 A | 2/1999 | Lazarus |
| 5,720,776 A | 2/1998 | Chuter et al. | 5,871,537 A | 2/1999 | Holman et al. |

| | | | | | | |
|---|---|---|---|---|---|---|
| 5,871,538 A | 2/1999 | Dereume | | 6,059,823 A | 5/2000 | Holman et al. |
| 5,873,906 A | 2/1999 | Lau et al. | | 6,060,534 A | 5/2000 | Ronan et al. |
| 5,876,432 A | 3/1999 | Lau et al. | | 6,063,114 A | 5/2000 | Nash et al. |
| 5,891,193 A | 4/1999 | Robinson et al. | | 6,068,626 A | 5/2000 | Harrington et al. |
| 5,904,713 A | 5/1999 | Leschinsky | | 6,070,589 A | 6/2000 | Keith et al. |
| 5,906,619 A | 5/1999 | Olson et al. | | 6,074,341 A | 6/2000 | Anderson et al. |
| 5,906,641 A | 5/1999 | Thompson et al. | | 6,075,180 A | 6/2000 | Sharber et al. |
| 5,910,168 A | 6/1999 | Meyers et al. | | 6,077,296 A | 6/2000 | Shokoohi et al. |
| 5,910,277 A | 6/1999 | Ishlno et al. | | 6,077,297 A | 6/2000 | Robinson et al. |
| 5,911,754 A | 6/1999 | Kanesaka et al. | | 6,077,298 A | 6/2000 | Tu et al. |
| 5,916,264 A | 6/1999 | Von Oepen et al. | | 6,090,128 A | 7/2000 | Douglas |
| 5,919,204 A | 7/1999 | Lukic et al. | | 6,093,203 A | 7/2000 | Uflacker |
| 5,922,020 A | 7/1999 | Klein et al. | | 6,096,052 A | 8/2000 | Callister et al. |
| 5,925,061 A | 7/1999 | Ogi et al. | | 6,096,070 A | 8/2000 | Ragheb et al. |
| 5,925,075 A | 7/1999 | Myers et al. | | 6,098,630 A | 8/2000 | Papazoglou |
| 5,931,865 A | 8/1999 | Silverman et al. | | 6,102,918 A | 8/2000 | Kerr |
| 5,935,667 A | 8/1999 | Calcote et al. | | 6,102,938 A | 8/2000 | Evans et al. |
| 5,939,198 A | 8/1999 | Howard, Jr. et al. | | 6,102,940 A | 8/2000 | Robichon et al. |
| 5,944,750 A | 8/1999 | Tanner et al. | | 6,103,172 A | 8/2000 | Newman et al. |
| 5,948,016 A | 9/1999 | Jang | | 6,106,548 A | 8/2000 | Roubin et al. |
| 5,954,729 A | 9/1999 | Bachmann et al. | | 6,110,198 A | 8/2000 | Fogarty et al. |
| 5,955,016 A | 9/1999 | Goldfarb | | 6,113,628 A | 9/2000 | Borghi |
| 5,957,973 A | 9/1999 | Quiachon et al. | | 6,117,168 A | 9/2000 | Yang et al. |
| 5,961,545 A | 10/1999 | Lentz et al. | | 6,123,722 A | 9/2000 | Fogarty et al. |
| 5,961,546 A | 10/1999 | Robinson et al. | | 6,124,523 A | 9/2000 | Banas et al. |
| 5,968,068 A | 10/1999 | Dehdashtian et al. | | 6,126,685 A | 10/2000 | Lenker et al. |
| 5,968,090 A | 10/1999 | Ratcliff et al. | | 6,129,756 A | 10/2000 | Kugler et al. |
| 5,972,023 A | 10/1999 | Tanner et al. | | 6,132,457 A | 10/2000 | Chobotov |
| 5,972,027 A | 10/1999 | Johnson | | 6,132,459 A | 10/2000 | Piplani et al. |
| 5,972,441 A | 10/1999 | Campbell et al. | | 6,139,572 A | 10/2000 | Campbell et al. |
| 5,976,155 A | 11/1999 | Foreman et al. | | 6,142,973 A | 11/2000 | Carleton et al. |
| 5,976,179 A | 11/1999 | Inoue | | 6,143,014 A | 11/2000 | Dehdashtian et al. |
| 5,976,192 A | 11/1999 | McIntyre et al. | | 6,143,015 A | 11/2000 | Nobles |
| 5,976,650 A | 11/1999 | Campbell et al. | | 6,143,016 A | 11/2000 | Bleam et al. |
| 5,980,530 A | 11/1999 | Willard et al. | | 6,143,021 A | 11/2000 | Staehle |
| 5,980,570 A | 11/1999 | Simpson | | 6,143,022 A | 11/2000 | Shull et al. |
| 5,984,955 A | 11/1999 | Wisselink | | 6,146,389 A | 11/2000 | Geitz |
| 5,984,956 A | 11/1999 | Tweden et al. | | 6,146,416 A | 11/2000 | Andersen et al. |
| 5,984,964 A | 11/1999 | Roberts et al. | | 6,146,417 A | 11/2000 | Ischinger |
| 5,989,287 A | 11/1999 | Yang et al. | | 6,149,665 A | 11/2000 | Gabbay |
| 5,993,481 A | 11/1999 | Marcade et al. | | 6,149,681 A | 11/2000 | Houser et al. |
| 5,993,489 A | 11/1999 | Lewis et al. | | 6,149,682 A | 11/2000 | Frid |
| 5,997,573 A | 12/1999 | Quijano et al. | | 6,152,944 A | 11/2000 | Holman et al. |
| 6,001,123 A | 12/1999 | Lau | | 6,152,956 A | 11/2000 | Pierce |
| 6,004,346 A | 12/1999 | Wolff et al. | | 6,156,063 A | 12/2000 | Douglas |
| 6,004,347 A | 12/1999 | McNamara et al. | | 6,156,064 A | 12/2000 | Chouinard |
| 6,004,348 A | 12/1999 | Banas et al. | | 6,159,229 A | 12/2000 | Jendersee et al. |
| 6,007,575 A | 12/1999 | Samuels | | 6,159,237 A | 12/2000 | Alt et al. |
| 6,015,429 A | 1/2000 | Lau et al. | | 6,159,238 A | 12/2000 | Killion et al. |
| 6,015,431 A | 1/2000 | Thornton et al. | | 6,159,239 A | 12/2000 | Greenhalgh |
| 6,015,432 A | 1/2000 | Rakos et al. | | 6,159,565 A | 12/2000 | Campbell et al. |
| 6,017,362 A | 1/2000 | Lau | | 6,162,243 A | 12/2000 | Gray et al. |
| 6,017,364 A | 1/2000 | Lazarus | | 6,162,245 A | 12/2000 | Jayaraman |
| 6,019,778 A | 2/2000 | Wilson et al. | | 6,162,246 A | 12/2000 | Barone |
| 6,019,779 A | 2/2000 | Thorud et al. | | 6,165,210 A | 12/2000 | Lau et al. |
| 6,019,787 A | 2/2000 | Richard et al. | | 6,165,211 A | 12/2000 | Thompson |
| 6,022,359 A | 2/2000 | Frantzen | | 6,165,212 A | 12/2000 | Dereume et al. |
| 6,024,763 A | 2/2000 | Lenker et al. | | 6,165,213 A | 12/2000 | Goicoechea et al. |
| 6,025,044 A | 2/2000 | Campbell et al. | | 6,165,214 A | 12/2000 | Lazarus |
| 6,027,779 A | 2/2000 | Campbell et al. | | 6,168,610 B1 | 1/2001 | Marin et al. |
| 6,027,811 A | 2/2000 | Campbell et al. | | 6,168,614 B1 | 1/2001 | Andersen et al. |
| 6,030,413 A | 2/2000 | Lazarus | | 6,168,616 B1 | 1/2001 | Brown, III |
| 6,030,414 A | 2/2000 | Taheri | | 6,168,617 B1 | 1/2001 | Blaeser et al. |
| 6,030,415 A | 2/2000 | Chuter | | 6,168,618 B1 | 1/2001 | Frantzen |
| 6,036,640 A | 3/2000 | Corace et al. | | 6,168,619 B1 | 1/2001 | Dinh et al. |
| 6,036,702 A | 3/2000 | Bachinski et al. | | 6,168,620 B1 | 1/2001 | Kerr |
| 6,036,723 A | 3/2000 | Anidjar et al. | | 6,174,326 B1 | 1/2001 | Kitaoka et al. |
| 6,036,724 A | 3/2000 | Lentz et al. | | 6,183,481 B1 | 2/2001 | Lee et al. |
| 6,036,725 A | 3/2000 | Avellanet | | 6,183,504 B1 | 2/2001 | Inoue |
| 6,039,754 A | 3/2000 | Caro | | 6,187,034 B1 | 2/2001 | Frantzen |
| 6,039,758 A | 3/2000 | Quiachon et al. | | 6,187,036 B1 | 2/2001 | Shaolian et al. |
| 6,042,589 A | 3/2000 | Marianne | | 6,187,054 B1 | 2/2001 | Colone et al. |
| 6,042,605 A | 3/2000 | Martin et al. | | 6,193,745 B1 | 2/2001 | Fogarty et al. |
| 6,042,606 A | 3/2000 | Frantzen | | 6,196,230 B1 | 3/2001 | Hall et al. |
| 6,045,557 A | 4/2000 | White et al. | | 6,197,046 B1 | 3/2001 | Piplani et al. |
| 6,048,484 A | 4/2000 | House et al. | | 6,197,049 B1 | 3/2001 | Shaolian et al. |
| 6,051,020 A | 4/2000 | Goicoechea et al. | | 6,200,339 B1 | 3/2001 | Leschinsky et al. |
| 6,053,943 A | 4/2000 | Edwin et al. | | 6,203,550 B1 | 3/2001 | Olson |
| 6,059,821 A | 5/2000 | Anidjar et al. | | 6,203,568 B1 | 3/2001 | Lombardi et al. |

| | | | | | | |
|---|---|---|---|---|---|---|
| 6,203,569 B1 | 3/2001 | Wijay | | 6,331,188 B1 | 12/2001 | Lau et al. |
| 6,203,735 B1 | 3/2001 | Edwin et al. | | 6,331,190 B1 | 12/2001 | Shokoohi et al. |
| 6,203,779 B1 | 3/2001 | Ricci et al. | | 6,331,191 B1 | 12/2001 | Chobotov |
| 6,210,422 B1 | 4/2001 | Douglas | | 6,334,869 B1 | 1/2002 | Leonhardt et al. |
| 6,210,434 B1 | 4/2001 | Quiachon et al. | | 6,336,937 B1 | 1/2002 | Vonesh et al. |
| 6,210,435 B1 | 4/2001 | Piplani et al. | | 6,344,044 B1 | 2/2002 | Fulkerson et al. |
| 6,214,038 B1 | 4/2001 | Piplani et al. | | 6,344,054 B1 | 2/2002 | Parodi |
| 6,214,039 B1 | 4/2001 | Banas et al. | | 6,344,055 B1 | 2/2002 | Shukov |
| 6,217,608 B1 | 4/2001 | Penn et al. | | 6,346,118 B1 | 2/2002 | Baker et al. |
| 6,221,102 B1 | 4/2001 | Baker et al. | | 6,346,119 B1 | 2/2002 | Kuwahara et al. |
| 6,224,609 B1 | 5/2001 | Ressemann et al. | | 6,348,065 B1 | 2/2002 | Brown et al. |
| 6,231,562 B1 | 5/2001 | Khosravi et al. | | 6,350,277 B1 | 2/2002 | Kocur |
| 6,235,050 B1 | 5/2001 | Quiachon et al. | | 6,352,553 B1 | 3/2002 | Van der Burg et al. |
| 6,235,051 B1 | 5/2001 | Murphy | | 6,352,561 B1 | 3/2002 | Leopold et al. |
| 6,238,432 B1 | 5/2001 | Parodi | | 6,355,055 B1 | 3/2002 | Waksman et al. |
| 6,240,616 B1 | 6/2001 | Yan | | 6,355,056 B1 | 3/2002 | Pnheiro |
| 6,241,759 B1 | 6/2001 | Piplani et al. | | 6,355,060 B1 | 3/2002 | Lenker et al. |
| 6,245,097 B1 | 6/2001 | Inoue | | 6,355,063 B1 | 3/2002 | Calcote |
| 6,245,099 B1 | 6/2001 | Edwin et al. | | 6,357,104 B1 | 3/2002 | Myers |
| 6,245,100 B1 | 6/2001 | Davila et al. | | 6,358,276 B1 | 3/2002 | Edwin et al. |
| 6,245,101 B1 | 6/2001 | Drasler et al. | | 6,358,284 B1 | 3/2002 | Fearnot et al. |
| 6,245,102 B1 | 6/2001 | Jayaraman | | 6,361,637 B2 | 3/2002 | Martin et al. |
| 6,248,116 B1 | 6/2001 | Chevillon et al. | | 6,363,938 B2 | 4/2002 | Saadat |
| 6,251,132 B1 | 6/2001 | Ravenscroft et al. | | 6,364,856 B1 | 4/2002 | Ding et al. |
| 6,251,136 B1 | 6/2001 | Guruwaiya et al. | | 6,364,904 B1 | 4/2002 | Smith |
| 6,254,593 B1 | 7/2001 | Wilson | | 6,368,346 B1 | 4/2002 | Jadhav |
| 6,254,632 B1 | 7/2001 | Wu et al. | | 6,368,347 B1 | 4/2002 | Maini et al. |
| 6,258,073 B1 | 7/2001 | Mauch | | 6,368,355 B1 | 4/2002 | Uflacker |
| 6,258,114 B1 | 7/2001 | Konya et al. | | 6,371,979 B1 | 4/2002 | Beyar et al. |
| 6,258,116 B1 | 7/2001 | Hojeibane | | 6,372,136 B1 | 4/2002 | Nakatsuka |
| 6,261,316 B1 | 7/2001 | Shaolian et al. | | 6,375,787 B1 | 4/2002 | Lukic |
| 6,261,317 B1 | 7/2001 | Inoue | | 6,379,381 B1 | 4/2002 | Hossainy et al. |
| 6,264,662 B1 | 7/2001 | Lauterjung | | 6,379,382 B1 | 4/2002 | Yang |
| 6,264,684 B1 | 7/2001 | Banas et al. | | 6,379,392 B1 | 4/2002 | Walak |
| 6,267,783 B1 | 7/2001 | Letendre et al. | | 6,383,213 B2 | 5/2002 | Wilson et al. |
| 6,267,834 B1 | 7/2001 | Shannon et al. | | 6,383,214 B1 | 5/2002 | Banas et al. |
| 6,270,524 B1 | 8/2001 | Kim | | 6,387,119 B2 | 5/2002 | Wolf et al. |
| 6,270,525 B1 | 8/2001 | Letendre et al. | | 6,387,124 B1 | 5/2002 | Buscemi et al. |
| 6,270,707 B1 | 8/2001 | Hori et al. | | 6,391,050 B1 | 5/2002 | Broome |
| 6,273,909 B1 | 8/2001 | Kugler et al. | | 6,391,052 B2 | 5/2002 | Buirge et al. |
| 6,273,910 B1 | 8/2001 | Limon | | 6,395,019 B2 | 5/2002 | Chobotov |
| 6,273,911 B1 | 8/2001 | Cox et al. | | 6,395,022 B1 | 5/2002 | Piplani et al. |
| 6,280,457 B1 | 8/2001 | Wallace et al. | | 6,395,208 B1 | 5/2002 | Herweck et al. |
| 6,280,466 B1 | 8/2001 | Kugleret al. | | 6,398,803 B1 | 6/2002 | Layne et al. |
| 6,280,467 B1 | 8/2001 | Leonhardt et al. | | 6,402,779 B1 | 6/2002 | Colone et al. |
| 6,283,991 B1 | 9/2001 | Cox et al. | | 6,406,489 B1 | 6/2002 | Richter et al. |
| 6,287,315 B1 | 9/2001 | Wijeratne et al. | | 6,409,749 B1 | 6/2002 | Maynard |
| 6,287,329 B1 | 9/2001 | Duarig et al. | | 6,409,750 B1 | 6/2002 | Hyodoh et al. |
| 6,287,330 B1 | 9/2001 | Johansson et al. | | 6,409,754 B1 | 6/2002 | Smith et al. |
| 6,287,335 B1 | 9/2001 | Drasler et al. | | 6,409,756 B1 | 6/2002 | Murphy |
| 6,287,336 B1 | 9/2001 | Globerman et al. | | 6,409,757 B1 | 6/2002 | Trout et al. |
| 6,290,728 B1 | 9/2001 | Phelps et al. | | 6,409,761 B1 | 6/2002 | Jang |
| 6,293,966 B1 | 9/2001 | Frantzen | | 6,413,269 B1 | 7/2002 | Bui et al. |
| 6,293,968 B1 | 9/2001 | Taheri | | 6,416,535 B1 | 7/2002 | Lazarus |
| 6,293,969 B1 | 9/2001 | Chuter | | 6,416,536 B1 | 7/2002 | Yee |
| 6,296,661 B1 | 10/2001 | Davila et al. | | 6,416,537 B1 | 7/2002 | Martakos et al. |
| 6,302,891 B1 | 10/2001 | Nadal | | 6,416,538 B1 | 7/2002 | Ley et al. |
| 6,302,905 B1 | 10/2001 | Goldsteen et al. | | 6,416,539 B1 | 7/2002 | Hassdenteufel |
| 6,302,906 B1 | 10/2001 | Goicoechea et al. | | 6,416,542 B1 | 7/2002 | Marcade et al. |
| 6,302,908 B1 | 10/2001 | Parodi | | 6,419,701 B1 | 7/2002 | Cook et al. |
| 6,303,100 B1 | 10/2001 | Ricci et al. | | 6,423,084 B1 | 7/2002 | St. Germain |
| 6,306,141 B1 | 10/2001 | Jervis | | 6,423,089 B1 | 7/2002 | Gingras et al. |
| 6,306,145 B1 | 10/2001 | Laschinsky | | 6,423,090 B1 | 7/2002 | Hancock |
| 6,306,164 B1 | 10/2001 | Kujawski | | 6,425,855 B2 | 7/2002 | Tomonto |
| 6,306,165 B1 | 10/2001 | Patnaik et al. | | 6,425,898 B1 | 7/2002 | Wilson et al. |
| 6,312,458 B1 | 11/2001 | Golds | | 6,428,506 B1 | 8/2002 | Simhambhatla et al. |
| 6,312,460 B2 | 11/2001 | Drasler et al. | | 6,428,565 B1 | 8/2002 | Wisselink |
| 6,312,462 B1 | 11/2001 | McDermott et al. | | 6,428,566 B1 | 8/2002 | Holt |
| 6,315,791 B1 | 11/2001 | Gingras et al. | | 6,428,567 B2 | 8/2002 | Wilson et al. |
| 6,319,276 B1 | 11/2001 | Holman et al. | | 6,428,569 B1 | 8/2002 | Brown |
| 6,319,278 B1 | 11/2001 | Quinn | | 6,428,570 B1 | 8/2002 | Globerman |
| 6,319,279 B1 | 11/2001 | Shannon et al. | | 6,428,571 B1 | 8/2002 | Lentz et al. |
| 6,322,587 B1 | 11/2001 | Quiachon et al. | | 6,432,129 B2 | 8/2002 | DiCaprio |
| 6,325,819 B1 | 12/2001 | Pavcnik et al. | | 6,432,131 B1 | 8/2002 | Ravenscroft |
| 6,325,823 B1 | 12/2001 | Horzewski et al. | | 6,432,132 B1 | 8/2002 | Cottone et al. |
| 6,325,824 B2 | 12/2001 | Limon | | 6,436,104 B2 | 8/2002 | Hoieibane |
| 6,325,825 B1 | 12/2001 | Kula et al. | | 6,436,133 B1 | 8/2002 | Furst et al. |
| 6,328,762 B1 | 12/2001 | Anderson et al. | | 6,436,134 B2 | 8/2002 | Richter et al. |
| 6,331,186 B1 | 12/2001 | Wang et al. | | 6,436,135 B1 | 8/2002 | Goldfarb |

| Patent | Date | Inventor |
|---|---|---|
| 6,440,165 B1 | 8/2002 | Richter et al. |
| 6,443,941 B1 | 9/2002 | Slepian et al. |
| 6,443,979 B1 | 9/2002 | Stalker et al. |
| 6,443,981 B1 | 9/2002 | Colone et al. |
| 6,447,501 B1 | 9/2002 | Solar et al. |
| 6,447,522 B2 | 9/2002 | Gambale et al. |
| 6,451,047 B2 | 9/2002 | McCrea et al. |
| 6,451,050 B1 | 9/2002 | Rudakov et al. |
| 6,451,053 B1 | 9/2002 | Dehdashtian et al. |
| 6,454,796 B1 | 9/2002 | Barkman et al. |
| 6,461,381 B2 | 10/2002 | Israel et al. |
| 6,464,720 B2 | 10/2002 | Boatman et al. |
| 6,464,721 B1 | 10/2002 | Marcade et al. |
| 6,464,722 B2 | 10/2002 | Israel et al. |
| 6,471,718 B1 | 10/2002 | Staehle et al. |
| 6,471,720 B1 | 10/2002 | Ehr et al. |
| 6,471,721 B1 | 10/2002 | Dang |
| 6,471,722 B1 | 10/2002 | Inoue |
| 6,475,166 B1 | 11/2002 | Escano |
| 6,475,208 B2 | 11/2002 | Mauch |
| 6,475,236 B1 | 11/2002 | Roubin et al. |
| 6,475,237 B2 | 11/2002 | Drasler |
| 6,475,238 B1 | 11/2002 | Fedida |
| 6,475,466 B1 | 11/2002 | Ricci et al. |
| 6,478,807 B1 | 11/2002 | Foreman et al. |
| 6,478,815 B1 | 11/2002 | Alt |
| 6,478,816 B1 | 11/2002 | Kveen et al. |
| 6,482,227 B1 | 11/2002 | Solovay |
| 6,485,507 B1 | 11/2002 | Walak et al. |
| 6,485,508 B1 | 11/2002 | McGuinness |
| 6,485,509 B2 | 11/2002 | Killion et al. |
| 6,485,511 B2 | 11/2002 | Lau et al. |
| 6,485,513 B1 | 11/2002 | Fan |
| 6,485,515 B2 | 11/2002 | Strecker |
| 6,485,524 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,488,705 B2 | 12/2002 | Schmitt et al. |
| 6,491,718 B1 | 12/2002 | Ahmad |
| 6,491,719 B1 | 12/2002 | Fogary et al. |
| 6,494,875 B1 | 12/2002 | Mauch |
| 6,494,904 B1 | 12/2002 | Love |
| 6,494,907 B1 | 12/2002 | Bulver |
| 6,494,909 B2 | 12/2002 | Greenhalgh |
| 6,497,722 B1 | 12/2002 | Von Oepen et al. |
| 6,497,723 B1 | 12/2002 | Starck et al. |
| 6,500,202 B1 | 12/2002 | Shaolian et al. |
| 6,500,203 B1 | 12/2002 | Thompson et al. |
| 6,500,204 B1 | 12/2002 | Igaki |
| 6,500,532 B1 | 12/2002 | Ruefer et al. |
| 6,503,271 B2 | 1/2003 | Duerig et al. |
| 6,506,211 B1 | 1/2003 | Doran et al. |
| 6,508,833 B2 | 1/2003 | Pavcnik et al. |
| 6,508,834 B1 | 1/2003 | Pinchasik et al. |
| 6,514,281 B1 | 2/2003 | Blaeser et al. |
| 6,517,558 B2 | 2/2003 | Gittings et al. |
| 6,517,571 B1 | 2/2003 | Brauker et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,520,986 B2 | 2/2003 | Martin et al. |
| 6,524,334 B1 | 2/2003 | Thompson |
| 6,524,335 B1 | 2/2003 | Hartley et al. |
| 6,524,336 B1 | 2/2003 | Papazolgou et al. |
| 6,530,765 B1 | 3/2003 | Zdrahala et al. |
| 6,530,947 B1 | 3/2003 | Euteneuer et al. |
| 6,530,950 B1 | 3/2003 | Alvarado et al. |
| 6,533,806 B1 | 3/2003 | Sullivan et al. |
| 6,533,807 B2 | 3/2003 | Wolinsky et al. |
| 6,533,808 B1 | 3/2003 | Thompson |
| 6,533,811 B1 | 3/2003 | Ryan et al. |
| 6,537,202 B1 | 3/2003 | Frantzen |
| 6,540,778 B1 | 4/2003 | Quiachon et al. |
| 6,540,780 B1 | 4/2003 | Zilla et al. |
| 6,547,813 B2 | 4/2003 | Stiger et al. |
| 6,547,814 B2 | 4/2003 | Edwin et al. |
| 6,547,815 B2 | 4/2003 | Myers |
| 6,547,817 B1 | 4/2003 | Fischell et al. |
| 6,548,013 B2 | 4/2003 | Kadavy et al. |
| 6,551,350 B1 | 4/2003 | Thornton et al. |
| 6,554,857 B1 | 4/2003 | Zilla et al. |
| 6,554,858 B2 | 4/2003 | Dereume et al. |
| 6,558,414 B2 | 5/2003 | Layne |
| 6,558,415 B2 | 5/2003 | Thompson |
| 6,562,063 B1 | 5/2003 | Euteneuer et al. |
| 6,565,597 B1 | 5/2003 | Fearnot |
| 6,569,150 B2 | 5/2003 | Teague |
| 6,569,190 B2 | 5/2003 | Whalen, II et al. |
| 6,569,193 B1 | 5/2003 | Cox et al. |
| 6,572,649 B2 | 6/2003 | Berry et al. |
| 6,575,994 B1 | 6/2003 | Marin |
| 6,576,009 B2 | 6/2003 | Ryan et al. |
| 6,579,314 B1 | 6/2003 | Lombardi et al. |
| 6,582,458 B1 | 6/2003 | White et al. |
| 6,589,274 B2 | 7/2003 | Stiger et al. |
| 6,589,275 B1 | 7/2003 | Ivancev et al. |
| 6,592,614 B2 | 7/2003 | Lenker et al. |
| 6,602,269 B2 | 8/2003 | Wallace et al. |
| 6,602,280 B2 | 8/2003 | Chobotov |
| 6,602,283 B2 | 8/2003 | Doran et al. |
| 6,605,110 B2 | 8/2003 | Harrison |
| 6,607,551 B1 | 8/2003 | Sullivan et al. |
| 6,613,082 B2 | 9/2003 | Yang |
| 6,613,083 B2 | 9/2003 | Alt |
| 6,613,084 B2 | 9/2003 | Yang |
| 6,620,190 B1 | 9/2003 | Colone |
| 6,626,938 B1 | 9/2003 | Butaric et al. |
| 6,635,079 B2 | 10/2003 | Unsworth et al. |
| 6,645,240 B2 | 11/2003 | Yee |
| 6,652,554 B1 | 11/2003 | Wholey et al. |
| 6,652,570 B2 | 11/2003 | Smith et al. |
| 6,652,573 B2 | 11/2003 | Oepen |
| 6,652,575 B2 | 11/2003 | Wang |
| 6,652,580 B1 | 11/2003 | Chutter |
| 6,656,215 B1 | 12/2003 | Yanez et al. |
| 6,656,506 B1 | 12/2003 | Wu et al. |
| 6,660,030 B2 | 12/2003 | Shaolian et al. |
| 6,663,662 B2 | 12/2003 | Pacetti et al. |
| 6,663,663 B2 | 12/2003 | Kim et al. |
| 6,663,665 B2 | 12/2003 | Shaolian et al. |
| 6,663,667 B2 | 12/2003 | Dehdashtian et al. |
| 6,669,720 B1 | 12/2003 | Pierce |
| 6,669,723 B2 | 12/2003 | Killion et al. |
| 6,669,724 B2 | 12/2003 | Park et al. |
| 6,673,102 B1 | 1/2004 | Vonesh et al. |
| 6,673,103 B1 | 1/2004 | Golds et al. |
| 6,673,106 B2 | 1/2004 | Mitelberg et al. |
| 6,673,107 B1 | 1/2004 | Brandt et al. |
| 6,676,667 B2 | 1/2004 | Mareiro et al. |
| 6,676,695 B2 | 1/2004 | Solem |
| 6,679,911 B2 | 1/2004 | Burgermeister |
| 6,685,736 B1 | 2/2004 | White et al. |
| 6,689,158 B1 | 2/2004 | White et al. |
| 6,689,159 B2 | 2/2004 | Hartigan et al. |
| 6,692,523 B2 | 2/2004 | Holman et al. |
| 6,694,983 B2 | 2/2004 | Wolf et al. |
| 6,695,833 B1 | 2/2004 | Frantzen |
| 6,695,875 B2 | 2/2004 | Stelter et al. |
| 6,695,877 B2 | 2/2004 | Brucker et al. |
| 6,696,666 B2 | 2/2004 | Merdan et al. |
| 6,699,274 B2 | 3/2004 | Stinson |
| 6,699,277 B1 | 3/2004 | Freidberg et al. |
| 6,702,847 B2 | 3/2004 | DiCarlo |
| 6,702,849 B1 | 3/2004 | Dutta et al. |
| 6,706,064 B1 | 3/2004 | Anson |
| 6,709,449 B2 | 3/2004 | Camrud et al. |
| 6,709,455 B1 | 3/2004 | Chouinard |
| 6,712,827 B2 | 3/2004 | Ellis et al. |
| 6,716,238 B2 | 4/2004 | Elliott |
| 6,716,239 B2 | 4/2004 | Sowinski |
| 6,719,783 B2 | 4/2004 | Lentz et al. |
| 6,726,712 B1 | 4/2004 | Raeder-Devens |
| 6,730,119 B1 | 5/2004 | Smalling |
| 6,733,521 B2 | 5/2004 | Chobotov et al. |
| 6,736,839 B2 | 5/2004 | Cummings |
| 6,740,111 B1 | 5/2004 | Lauterjung |

| | | |
|---|---|---|
| 6,740,114 B2 | 5/2004 | Burgermeister |
| 6,740,115 B2 | 5/2004 | Lombardi |
| 6,743,210 B2 | 6/2004 | Hart et al. |
| 6,743,511 B2 | 6/2004 | Dittrich et al. |
| 6,746,890 B2 | 6/2004 | Gupta |
| 6,752,829 B2 | 6/2004 | Kocur et al. |
| 6,755,855 B2 | 6/2004 | Yurek et al. |
| 6,758,858 B2 | 7/2004 | McCrea et al. |
| 6,761,733 B2 | 7/2004 | Chobotov et al. |
| 6,770,086 B1 | 8/2004 | Girton et al. |
| 6,770,087 B2 | 8/2004 | Layne et al. |
| 6,773,453 B2 | 8/2004 | Ravenscroft |
| 6,773,457 B2 | 8/2004 | Ivancev et al. |
| 6,776,604 B1 | 8/2004 | Chobotov et al. |
| 6,776,793 B2 | 8/2004 | Brown et al. |
| 6,786,920 B2 | 9/2004 | Shannon et al. |
| 6,790,227 B2 | 9/2004 | Burgermeister |
| 6,790,230 B2 | 9/2004 | Beyersdorf et al. |
| 6,793,672 B2 | 9/2004 | Khosravi et al. |
| 6,796,999 B2 | 9/2004 | Pinchasik |
| 6,802,849 B2 | 10/2004 | Blaeser et al. |
| 6,802,856 B2 | 10/2004 | Wilson |
| 6,814,753 B2 | 11/2004 | Schmitt |
| 6,818,013 B2 | 11/2004 | Mitelberg et al. |
| 6,821,292 B2 | 11/2004 | Pazienza et al. |
| 6,824,558 B2 | 11/2004 | Parodi |
| 6,827,726 B2 | 12/2004 | Parodi |
| 6,827,731 B2 | 12/2004 | Armstrong et al. |
| 6,827,735 B2 | 12/2004 | Greenbeg |
| 6,827,737 B2 | 12/2004 | Hill et al. |
| 6,833,004 B2 | 12/2004 | Ishii et al. |
| 6,841,213 B2 | 1/2005 | Parsonage et al. |
| 6,843,802 B1 | 1/2005 | Villalobos et al. |
| 6,849,086 B2 | 2/2005 | Cragg |
| 6,858,035 B2 | 2/2005 | Whayne |
| 6,860,900 B2 | 3/2005 | Clerc et al. |
| 6,863,685 B2 | 3/2005 | Davila et al. |
| 6,869,443 B2 | 3/2005 | Buscemi et al. |
| 6,878,160 B2 | 4/2005 | Gilligan et al. |
| 6,878,161 B2 | 4/2005 | Lenker |
| 6,884,260 B2 | 4/2005 | Kugler et al. |
| 6,899,728 B1 | 5/2005 | Phillips et al. |
| 6,918,925 B2 | 7/2005 | Tehrani |
| 6,918,927 B2 | 7/2005 | Bates et al. |
| 6,923,827 B2 | 8/2005 | Campbell et al. |
| 6,926,732 B2 | 8/2005 | Derus et al. |
| 6,929,659 B2 | 8/2005 | Pinchuk |
| 6,929,709 B2 | 8/2005 | Smith |
| 6,939,370 B2 | 9/2005 | Hartley et al. |
| 6,939,374 B2 | 9/2005 | Banik et al. |
| 6,942,689 B2 | 9/2005 | Majercak |
| 6,945,989 B1 | 9/2005 | Rourke et al. |
| 6,945,992 B2 | 9/2005 | Goodson et al. |
| 6,949,120 B2 | 9/2005 | Kveen et al. |
| 6,962,602 B2 | 11/2005 | Vardi et al. |
| 6,962,603 B1 | 11/2005 | Brown |
| 6,964,677 B2 | 11/2005 | Osypka |
| 6,974,471 B2 | 12/2005 | Van Schie et al. |
| 6,974,472 B2 | 12/2005 | Hong et al. |
| 6,981,982 B2 | 1/2006 | Armstrong et al. |
| 6,989,026 B2 | 1/2006 | Richter et al. |
| 6,994,722 B2 | 2/2006 | DiCarlo |
| 6,997,945 B2 | 2/2006 | Germain |
| 6,998,060 B2 | 2/2006 | Tomonto |
| 7,001,407 B2 | 2/2006 | Hansen et al. |
| 7,001,419 B2 | 2/2006 | DiCaprio et al. |
| 7,001,431 B2 | 2/2006 | Bao et al. |
| 7,011,673 B2 | 3/2006 | Fischell et al. |
| 7,011,674 B2 | 3/2006 | Brenneman |
| 7,022,132 B2 | 4/2006 | Kocur |
| 7,022,135 B2 | 4/2006 | Zilla et al. |
| 7,033,389 B2 | 4/2006 | Sherry |
| 7,056,325 B1 | 6/2006 | Makower et al. |
| 7,056,336 B2 | 6/2006 | Armstrong et al. |
| 7,056,412 B2 | 6/2006 | Henderson |
| 7,066,951 B2 | 6/2006 | Chobotov |
| 7,073,504 B2 | 7/2006 | Callister et al. |
| 7,081,129 B2 | 7/2006 | Chobotov |
| 7,081,132 B2 | 7/2006 | Cook |
| 7,083,642 B2 | 8/2006 | Sirhan et al. |
| 7,090,693 B1 | 8/2006 | Chobotov et al. |
| 7,094,255 B2 | 8/2006 | Penn et al. |
| 7,108,715 B2 | 9/2006 | Brown et al. |
| 7,115,140 B2 | 10/2006 | Stoltze et al. |
| 7,125,464 B2 | 10/2006 | Chobotov et al. |
| 7,128,754 B2 | 10/2006 | Bolduc |
| 7,128,755 B2 | 10/2006 | Su et al. |
| 7,147,455 B2 | 12/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,160,318 B2 | 1/2007 | Greenberg et al. |
| 7,175,651 B2 | 2/2007 | Kerr |
| 7,175,652 B2 | 2/2007 | Cook et al. |
| 7,189,256 B2 | 3/2007 | Smith |
| 7,192,441 B2 | 3/2007 | Sherry |
| 7,223,280 B2 | 5/2007 | Anson et al. |
| 7,226,474 B2 | 6/2007 | Iancea et al. |
| 7,229,470 B2 | 6/2007 | Brown et al. |
| 7,232,459 B2 | 6/2007 | Greenberg |
| 7,244,242 B2 | 7/2007 | Freyman |
| 7,273,494 B2 | 9/2007 | Rolando et al. |
| 7,284,399 B1 * | 10/2007 | Sisco ............................. 70/16 |
| 7,294,147 B2 | 11/2007 | Hartley |
| 7,314,484 B2 | 1/2008 | Deem et al. |
| 7,338,518 B2 | 3/2008 | Chobotov |
| 7,351,256 B2 | 4/2008 | Hojeibane et al. |
| 7,425,219 B2 | 9/2008 | Quadri |
| 7,452,374 B2 | 11/2008 | Hain et al. |
| 7,465,270 B2 | 12/2008 | Li |
| 7,485,138 B2 | 2/2009 | Fearnot et al. |
| 7,491,230 B2 | 2/2009 | Holman et al. |
| 7,491,234 B2 | 2/2009 | Palasis et al. |
| 7,500,988 B1 | 3/2009 | Butaric et al. |
| 7,510,571 B2 | 3/2009 | Spiridigliozzi et al. |
| 7,520,890 B2 | 4/2009 | Phillips |
| 7,520,895 B2 | 4/2009 | Douglas et al. |
| 7,530,988 B2 | 5/2009 | Evans et al. |
| 7,550,004 B2 | 6/2009 | Bahaler et al. |
| 7,550,005 B2 | 6/2009 | Bates et al. |
| 7,556,645 B2 | 7/2009 | Lashinski et al. |
| 7,591,843 B1 | 9/2009 | Escano |
| 7,597,710 B2 | 10/2009 | Obermiller |
| 2001/0014794 A1 | 8/2001 | Moll |
| 2001/0029349 A1 | 10/2001 | Leschinsky |
| 2001/0039445 A1 | 11/2001 | Hall et al. |
| 2001/0041928 A1 | 11/2001 | Pavenik et al. |
| 2001/0044652 A1 | 11/2001 | Moore |
| 2001/0049534 A1 | 12/2001 | Lachat |
| 2002/0007193 A1 | 1/2002 | Tanner et al. |
| 2002/0011684 A1 | 1/2002 | Bahar et al. |
| 2002/0016626 A1 | 2/2002 | DiMatteo et al. |
| 2002/0019659 A1 | 2/2002 | Goicoechea et al. |
| 2002/0029051 A1 | 3/2002 | Callister et al. |
| 2002/0032408 A1 | 3/2002 | Parker et al. |
| 2002/0040236 A1 | 4/2002 | Lau et al. |
| 2002/0040237 A1 | 4/2002 | Lentz et al. |
| 2002/0042644 A1 | 4/2002 | Greenhalgh |
| 2002/0045931 A1 | 4/2002 | Sogard et al. |
| 2002/0045933 A1 | 4/2002 | Jang |
| 2002/0045934 A1 | 4/2002 | Jang |
| 2002/0045935 A1 | 4/2002 | Jang |
| 2002/0049487 A1 | 4/2002 | Lootz et al. |
| 2002/0049490 A1 | 4/2002 | Pollock et al. |
| 2002/0049493 A1 | 4/2002 | Jang |
| 2002/0052627 A1 | 5/2002 | Boylan et al. |
| 2002/0052644 A1 | 5/2002 | Shaolin et al. |
| 2002/0052649 A1 | 5/2002 | Greenhalgh |
| 2002/0055768 A1 | 5/2002 | Hess et al. |
| 2002/0065552 A1 | 5/2002 | Jayaraman et al. |
| 2002/0072792 A1 | 6/2002 | Burgermeister et al. |
| 2002/0072793 A1 | 6/2002 | Rolando et al. |
| 2002/0076542 A1 | 6/2002 | Kramer et al. |
| 2002/0077692 A1 | 6/2002 | Besselink |
| 2002/0082680 A1 | 6/2002 | Stanley et al. |
| 2002/0082682 A1 | 6/2002 | Barclay et al. |
| 2002/0082685 A1 | 6/2002 | Sirhan et al. |
| 2002/0095208 A1 | 7/2002 | Gregorich et al. |

| | | |
|---|---|---|
| 2002/0096252 A1 | 7/2002 | Lukic |
| 2002/0107561 A1 | 8/2002 | Pinheiro |
| 2002/0120321 A1 | 8/2002 | Gunderson et al. |
| 2002/0120327 A1 | 8/2002 | Cox et al. |
| 2002/0123790 A1 | 9/2002 | White et al. |
| 2002/0123791 A1 | 9/2002 | Harrison |
| 2002/0123796 A1 | 9/2002 | Majercak et al. |
| 2002/0143387 A1 | 10/2002 | Soetikno et al. |
| 2002/0147492 A1 | 10/2002 | Shokoohi et al. |
| 2002/0151953 A1 | 10/2002 | Chobotov et al. |
| 2002/0161376 A1 | 10/2002 | Barry et al. |
| 2002/0165603 A1 | 11/2002 | Thornton et al. |
| 2002/0169497 A1 | 11/2002 | Wholey et al. |
| 2002/0183826 A1 | 12/2002 | Dorn et al. |
| 2002/0183827 A1 | 12/2002 | Derus et al. |
| 2002/0188346 A1 | 12/2002 | Healy et al. |
| 2002/0188347 A1 | 12/2002 | Mathis |
| 2002/0193867 A1 | 12/2002 | Gladdish, Jr. et al. |
| 2002/0193872 A1 | 12/2002 | Trout et al. |
| 2002/0193873 A1 | 12/2002 | Brucker et al. |
| 2002/0198585 A1 | 12/2002 | Wisselink |
| 2002/0198587 A1 | 12/2002 | Greenberg et al. |
| 2003/0004560 A1 | 1/2003 | Chobotov et al. |
| 2003/0004565 A1 | 1/2003 | Harnek et al. |
| 2003/0009212 A1 | 1/2003 | Kerr |
| 2003/0014075 A1 | 1/2003 | Rosenbluth et al. |
| 2003/0040803 A1 | 2/2003 | Rioux et al. |
| 2003/0050684 A1 | 3/2003 | Abrams et al. |
| 2003/0068296 A1 | 4/2003 | Ricci et al. |
| 2003/0083736 A1 | 5/2003 | Brown et al. |
| 2003/0097170 A1 | 5/2003 | Friedrich et al. |
| 2003/0120263 A1 | 6/2003 | Ouriel et al. |
| 2003/0120331 A1 | 6/2003 | Chobotov et al. |
| 2003/0125797 A1 | 7/2003 | Chobotov |
| 2003/0135256 A1 | 7/2003 | Gallagher et al. |
| 2003/0135261 A1 | 7/2003 | Kugler et al. |
| 2003/0176912 A1 | 9/2003 | Chuter et al. |
| 2003/0191518 A1 | 10/2003 | Spiridigliozzi et al. |
| 2003/0204236 A1 | 10/2003 | Letort |
| 2003/0204244 A1 | 10/2003 | Stiger |
| 2003/0220683 A1 | 11/2003 | Minasian |
| 2003/0225453 A1 | 12/2003 | Murch |
| 2004/0024446 A1 | 2/2004 | Smith |
| 2004/0034407 A1 | 2/2004 | Sherry |
| 2004/0044395 A1 | 3/2004 | Nelson |
| 2004/0049212 A1 | 3/2004 | Whayne |
| 2004/0049264 A1 | 3/2004 | Sowinski et al. |
| 2004/0093055 A1 | 5/2004 | Bartorelli et al. |
| 2004/0093064 A1 | 5/2004 | Bosma |
| 2004/0093068 A1 | 5/2004 | Bergen et al. |
| 2004/0093078 A1 | 5/2004 | Moll et al. |
| 2004/0098096 A1 | 5/2004 | Eton |
| 2004/0106974 A1 | 6/2004 | Greenberg et al. |
| 2004/0116997 A1 | 6/2004 | Taylor et al. |
| 2004/0138734 A1* | 7/2004 | Chobotov et al. ............ 623/1.11 |
| 2004/0162607 A1 | 8/2004 | Masroor |
| 2004/0167614 A1 | 8/2004 | Anson |
| 2004/0210304 A1 | 10/2004 | Seguin et al. |
| 2004/0215213 A1 | 10/2004 | Dolan |
| 2004/0220664 A1 | 11/2004 | Chobotov |
| 2004/0254625 A1 | 12/2004 | Stephens |
| 2005/0033406 A1 | 2/2005 | Barnhart et al. |
| 2005/0049691 A1 | 3/2005 | Mercile et al. |
| 2005/0075715 A1 | 4/2005 | Borges et al. |
| 2005/0090804 A1 | 4/2005 | Chobotov et al. |
| 2005/0090901 A1 | 4/2005 | Studer |
| 2005/0158272 A1 | 7/2005 | Whirley et al. |
| 2005/0171593 A1 | 8/2005 | Whirley et al. |
| 2005/0177222 A1 | 8/2005 | Mead |
| 2005/0222669 A1 | 10/2005 | Purdy |
| 2005/0228484 A1 | 10/2005 | Stephens et al. |
| 2006/0009833 A1 | 1/2006 | Chobotov et al. |
| 2006/0020319 A1 | 1/2006 | Kim |
| 2006/0079952 A1 | 4/2006 | Kaplan et al. |
| 2006/0136047 A1 | 6/2006 | Obermiller et al. |
| 2006/0149364 A1 | 7/2006 | Walak et al. |
| 2006/0178732 A1 | 8/2006 | Chobotov et al. |
| 2006/0186143 A1 | 8/2006 | Argentine |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0233991 A1 | 10/2006 | Humphrey et al. |
| 2006/0287713 A1 | 12/2006 | Douglas et al. |
| 2006/0292206 A1 | 12/2006 | Kim et al. |
| 2007/0012396 A1 | 1/2007 | Chobotov et al. |
| 2007/0016281 A1 | 1/2007 | Melsheimer |
| 2007/0055347 A1 | 3/2007 | Arbefeuille |
| 2007/0112413 A1 | 5/2007 | Smith |
| 2007/0162106 A1 | 7/2007 | Evans et al. |
| 2007/0167901 A1 | 7/2007 | Herrig et al. |
| 2007/0203571 A1 | 8/2007 | Kaplan et al. |
| 2007/0219627 A1 | 9/2007 | Chu et al. |
| 2007/0239273 A1 | 10/2007 | Allen |
| 2007/0244539 A1 | 10/2007 | Lentz et al. |
| 2007/0276477 A1 | 11/2007 | Lee et al. |
| 2007/0282369 A1 | 12/2007 | Gilson et al. |
| 2008/0015687 A1 | 1/2008 | Lashinski et al. |
| 2008/0027529 A1 | 1/2008 | Hartley et al. |
| 2008/0051705 A1 | 2/2008 | Von Oepen et al. |
| 2008/0058920 A1 | 3/2008 | Kari |
| 2008/0114441 A1 | 5/2008 | Rust |
| 2008/0114442 A1 | 5/2008 | Mitchell et al. |
| 2008/0114443 A1 | 5/2008 | Mitchell |
| 2008/0172119 A1 | 7/2008 | Yamasaki et al. |
| 2008/0228255 A1 | 9/2008 | Rust |
| 2009/0036971 A1 | 2/2009 | Humphrey et al. |
| 2009/0042796 A1 | 2/2009 | Wallach et al. |
| 2009/0082841 A1 | 3/2009 | Zacharias et al. |
| 2009/0082842 A1 | 3/2009 | Glynn |
| 2009/0082845 A1 | 3/2009 | Chobotov et al. |
| 2009/0082846 A1 | 3/2009 | Chobotov et al. |
| 2009/0082847 A1 | 3/2009 | Zacharias et al. |
| 2009/0099649 A1 | 4/2009 | Chobotov et al. |
| 2009/0132020 A1 | 5/2009 | Watson |
| 2009/0132026 A1 | 5/2009 | Martin et al. |
| 2009/0171431 A1 | 7/2009 | Swanson et al. |
| 2009/0182406 A1 | 7/2009 | Eidenschink |
| 2009/0198267 A1 | 8/2009 | Evans et al. |
| 2009/0287145 A1 | 11/2009 | Cragg et al. |
| 2010/0211052 A1 | 8/2010 | Brown et al. |

FOREIGN PATENT DOCUMENTS

| | | |
|---|---|---|
| EP | 0714641 | 6/1996 |
| EP | 0775472 | 5/1997 |
| EP | 0792627 | 9/1997 |
| EP | 0808613 | 11/1997 |
| EP | 0819411 | 1/1998 |
| EP | 0943302 | 9/1999 |
| EP | 0997115 | 5/2000 |
| EP | 0480667 | 4/2001 |
| EP | 1093772 | 4/2001 |
| EP | A 1138280 | 10/2001 |
| EP | 0808140 | 12/2001 |
| EP | 1163991 | 12/2001 |
| EP | 1212991 | 6/2002 |
| EP | 1266636 | 12/2002 |
| EP | 1380270 | 1/2004 |
| EP | 1415617 | 4/2004 |
| JP | 49 042773 | 4/1974 |
| JP | 3109404 | 5/1991 |
| JP | 5161665 | 6/1993 |
| JP | 6100054 | 4/1994 |
| JP | 09117511 | 5/1997 |
| JP | 18-126862 | 6/2006 |
| JP | 18-136382 | 6/2006 |
| RU | 2029527 | 2/1995 |
| SU | 1217402 | 3/1986 |
| SU | 1237201 | 6/1986 |
| SU | 1237202 | 6/1986 |
| SU | 1273077 | 11/1986 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |
| SU | 1732964 | 5/1992 |

| | | |
|---|---|---|
| SU | 1768154 | 10/1992 |
| SU | 1812980 | 4/1993 |
| WO | WO 91/00792 | 1/1991 |
| WO | WO 92/22604 | 12/1992 |
| WO | WO 93/13824 | 7/1993 |
| WO | WO 93/19804 | 10/1993 |
| WO | WO 94/03127 | 2/1994 |
| WO | WO 95/03754 | 2/1995 |
| WO | WO 95/09586 | 4/1995 |
| WO | WO 96/14095 | 5/1996 |
| WO | WO 96/14808 | 5/1996 |
| WO | WO 97/07751 | 3/1997 |
| WO | WO 97/29716 | 8/1997 |
| WO | WO 98/06355 | 2/1998 |
| WO | WO 98/38947 | 9/1998 |
| WO | WO 98/41167 | 9/1998 |
| WO | WO 98/44870 | 10/1998 |
| WO | WO 98/44873 | 10/1998 |
| WO | WO 99/00073 | 1/1999 |
| WO | WO 99/26559 | 6/1999 |
| WO | WO 99/38455 | 8/1999 |
| WO | WO 99/43378 | 9/1999 |
| WO | WO 99/43379 | 9/1999 |
| WO | WO 00/10487 | 3/2000 |
| WO | WO 00/13613 | 3/2000 |
| WO | WO 00/42947 | 7/2000 |
| WO | WO 00/42948 | 7/2000 |
| WO | WO 00/44808 | 8/2000 |
| WO | WO 00/51522 | 9/2000 |
| WO | WO 00/67675 | 11/2000 |
| WO | WO 00/71179 | 11/2000 |
| WO | WO 01/05331 | 1/2001 |
| WO | WO 01/08599 | 2/2001 |
| WO | WO 01/15633 | 3/2001 |
| WO | WO 01/21108 | 3/2001 |
| WO | WO 01/30270 | 5/2001 |
| WO | WO 01/41675 | 6/2001 |
| WO | WO 01/56500 | 8/2001 |
| WO | WO 01/56504 | 8/2001 |
| WO | WO 01/58384 | 8/2001 |
| WO | WO 01/58387 | 8/2001 |
| WO | WO 01/66037 | 9/2001 |
| WO | WO 01/67993 | 9/2001 |
| WO | WO 01/74270 | 10/2001 |
| WO | WO 01/82836 | 11/2001 |
| WO | WO 02/36332 | 5/2002 |
| WO | WO 02/41804 | 5/2002 |
| WO | WO 02/078569 | 10/2002 |
| WO | WO 02/083038 | 10/2002 |
| WO | WO 02/100454 | 12/2002 |
| WO | WO 03/022180 | 3/2003 |
| WO | WO 03/053287 | 7/2003 |
| WO | WO 03/094795 | 11/2003 |
| WO | WO 03/094799 | 11/2003 |
| WO | WO 2004/002370 | 1/2004 |
| WO | WO 2004/002371 | 1/2004 |
| WO | WO 2004/017866 | 3/2004 |
| WO | WO2008/0115678 | 9/2008 |
| WO | WO 2009/042796 | 4/2009 |
| WO | WO 2009/086200 | 7/2009 |

OTHER PUBLICATIONS

The AneuRx® Stent Graft Treatment for TAA brochure, "An Endoluminal Solution for the Treatment of Descending Thoracic Aortic Aneurysms," Medtronic, Inc. 1999.

Blum et al. "Abdominal aortic aneurysms: preliminary technical and clinical results with transfemoral placement of endovascular self-expanding stent-grafts" Radiology 198(1):25-31 (1996). ;198(1):25-31 (1996).

Blum et al. "Endoluminal stent-grafts for infrarenal abdominal aortic aneurysms" N Engl J Med 336(1):13-20 (1997). ;336(1):13-20 (1997).

Campbell et al., "Balloon-Artery Interactions During Stent Placement: A Finite Element Analysis Approach to Pressure, Compliance, and Stent Design as Contributors to Vascular Injury"; 1999; American Heart Association; pp. 378-383.

Canero et al., "Optimal stent implantation: three-dimensional evaluation of the mutual position of stent and vessel via intracoronary echocardiography," Computers in Cardiology, 261-264 (Sep. 1999).

Cooley, Denton A., Surgical Treatment of Aortic Aneurysms (Book), W.B. Saunders Company, West Washington Square, PA (1986).

Donayre, et al., "Fillable endovascular aneurysm repair", Endovascular Today, p. 64-66, Jan. 2009.

Dumoulin C. et al., "Mechanical behavior modeling of balloon expandable stents." Journal of Biomechanics, vol. 33, No. 11, pp. 1461-1470 (available online: Sep. 8, 2000).

Elger et al. "The Influence of Shape on the Stresses in Model Abdominal Aortic Aneurysms," Transactions of the ASME 326:326-32 (1996).

Ernst "Current therapy for infrarenal aortic aneurysms" N Engl J Med 336(1):58-60 (1997).

Haimovitch, L. and Patierson, N., "Robust growth is forecast for endovascular repair of AAAs," the BBI Newsletter, vol. 26, No. 5, pp. 113-144, (May 2003).

How et al. "Mechanical Properties of Arteries and Arterial Grafts," Chapter 1 of Cardiovascular BIOMATERIALS Hasting, G.W. (ed.) London; New York: Springer-Verlag, 1992 pp. 1-35.

International Search Report and Written Opinion mailed on May 28, 2009 for International Application No. PCT/US2008/087831 filed on Dec. 19, 2008 and published as WO/2009/086200 on Jul. 9, 2009.

International Search Report and Written Opinion mailed on Mar. 26, 2009 for International Application No. PCT/US2008/077727 filed on Sep. 25, 2008 and published as WO/2009/042796 on Apr. 2, 2009.

Lakshmiraghavan, M. Mechanical Wall Stress in Abdominal Aortic Aneurysm: Towards the Development of a Clinical Tool to Predict Aneurysm Rupture. Submitted to the University of Pittsburgh, vol. 59/09-B of Dissertation Abstracts International p. 4948. 285 pages (1998).

Mandai, S. et al. (1992). "Direct Thrombosis of Aneurysms with Cellulose Acetate Polymer. Part I: Results of Thrombosis in Experimental Aneurysms," J. Neurosurgery 77:497-500.

Mirich et al., "Percutaneously Placed Endovascular Grafts for Aortic Aneurysms: Feasibility Study", Radiology, 170/3:1033-1037 (1989); 1033-1037 (1989).

Moore et al. "Transfemoral endovascular repair of abdominal aortic aneurysm: results of the North American EVT phase 1 trial" J Vasc Surg 23(4):543-553 (1996). ;23(4):543-553 (1996).

Mower et al. "Stress Distributions in Vascular Aneurysms: Factors Affecting Risk of Aneurysm Rupture," J. Surgical Research 55:151-61 (1993).

Parodi "Endovascular repair of abdominal aortic aneurysms and other arterial lesions" J Vasc Surg 21(4):549-557 (1995).;21(4):549-557 (1995).

Parodi et al., "Transfemoral intraluminal graft implantation for abdominal aortic aneurysms," Ann. Vasc. Surg., 5(6):491-499 (1991).

Perry, M. D. and Chang, R. T., "Finite Element Analysis of NI-TI Alloy Stent Deployment," Proceedings of the Second International Conference on SMST, Asilomar Conference Center, Pacific Grove CA. USA (1997).

Rogers et al., "Balloon-Artery Interactions During Stent Placement: A finite element analysis approach to pressure, compliance and stent design as contributors to vascular injury", 1999 American Heart Association pp. 378-383.

Stern et al., "Interactive Definition of Endoluminal Aortic Stent Size and Morphology Based on Virtual Angioscopic Rendering of 3D Magnetic Resonance Angiography (MRA)," Cars. Computer Assisted Radiology and Surgery, Proceedings of the International Symposium on Computer Assisted Radiology and Surgery:176-180 (Jun. 1999).

Uflacker, R. and Robinson, J., "Endovascular treatment of abdominal aortic aneurysms: a review," Eur. Radial.,11:739-753 (2001).

Verhagen "Latest AAA Innovations: The Endurant Stent Graft System", Veith Symposium Nov. 17, 2007.

Verhagen, Hence J.M. "Endurant Medtronic Endograft for EVAR: advantages & early experience", Slides from Veith Symposium Presentation Nov. 22, 2008.

Vos A.F.W. et al., "Endovascular Grafting of Complex Aortic Aneurysms with a modular site Branch Stent Graft System in a Porcine Model", Eur J Vasc Endovasc Surg, May 2004 vol. 27 492-497.

Volodos, N.L. et al. (1987). "New Balloon Catheter for Dilating Arteries and Installing Prosthesis During Distal Endoprosthetics With Self-Fixing Synthetic Prosthesis," *Thesis of VIII Symposium* (Oct. 8-10, 1987), Abstract Only in English, four pages.

Volodos, N.L. et al. (1986) "Self-Fixing Synthetic Prostheisis for Endoprosthesis of Vessels," Vestnik Khigurgii pp. 123-124, Abstract Only in English.

Volodos, N.L. et al. (1989). "Clinical Experience in Use of Self-Fixing Synthetic Prosthesis For Distal and Intraoperative Endoprosthestics of Aora and Iliac Arteries," Theses of Ixth All-Union Symposium (Oct. 2-3, 1989), Abstract only in English, four pages.

Web page, "Drug Eluting Stents—Why Use Drug Eluting Stents?" Polymer Coatings Division; at: URLhttp://www.lombardmedlcal.co.uk/lombard/pcde.why.html; Lombard Medical; printed Feb. 1, 2005.

Whitcher, "Simulation of in vivo loading conditions of nitinol vascular stent structures", 1997, Elsevier Science Ltd., pp. 1005-1011.

Whitcher, F., "A Finite Element Treatment of the In-Vivo Loading Conditions of NITI AD Vascular Stent and Graft Structures," Proceedings of the Second International Conference on SMST, Asilomar Conference Center, Pacific Grove. CA, USA (1997).

Wisselink, W. et al. (2001). "Clipping of Inferior Mesenteric and Lumbar Arteries via Retroperitoneal Laparo-Endoscopic Approach as a Treatment of Persistent Endoleak" Chapter 18 in Endoleaks and Endotension, Veith, F.J. et al. eds. Marcel Dekker, Inc. pp. 211-220.

Extended European Search Report Mailed Jul. 27, 2010 in European Application No. 10005904.7 filed: Apr. 11, 2002 and published as: EP 2221023 on Aug. 25, 2010.

Extended European Search Report Mailed Dec. 16, 2009 in European Application No. 09175398.8 filed: Oct. 15, 2004 and published as: EP 2145607 on Jan. 20, 2010.

International Preliminary Report on Patentability mailed on Apr. 15, 2010 for International Application No. PCT/US2008/078846 filed on Oct. 3, 2008 and published as WO/2009/046372 on Apr. 9, 2009.

International Search Report and Written Opinion mailed on Jul. 30, 2009 for International Application No. PCT/US2008/078846 filed on Oct. 3, 2008 and published as WO/2009/046372 on Apr. 9, 2009.

International Preliminary Report on Patentability mailed on Apr. 8, 2010 for International Application No. PCT/US2008/077714 filed on Sep. 25, 2008 and published as WO/2009/042789 on Apr. 2, 2009.

International Search Report and Written Opinion mailed on: May 1, 2009 for International Application No. PCT/US2008/077714 filed on Sep. 25, 2008 and published as WO/2009/042789 on Apr. 2, 2009.

International Preliminary Report on Patentability mailed on May 27, 2010 for International Application No. PCT/US2008/083451 filed on Nov. 13, 2008 and published as WO/2009/064923 on May 22, 2009.

International Search Report and Written Opinion May 1, 2009 mailed on Jun. 30, 2009 for International Application No. PCT/US2008/083451 filed on Nov. 13, 2008 and published as WO/2009/064923 on May 22, 2009.

Office Action mailed on: Jan. 3, 2011 for U.S. Appl. No. 11/941,434, filed on Nov. 16, 2007 and published as US2009/0132026 on May 21, 2009.

US 6,413,270, 07/2002, Thornton et al. (withdrawn)

* cited by examiner

SECUREMENT ASSEMBLY AND METHOD FOR EXPANDABLE ENDOVASCULAR DEVICE

BACKGROUND OF THE INVENTION

This invention relates generally to endoluminal devices, particularly stents and grafts for placement in an area of a body lumen that has been weakened by damage or disease, such as an aneurysm of the abdominal aorta, and more particularly to a stent and a corresponding system for deployment thereof.

Medical devices for placement in a human or other animal body are well known in the art. One class of medical devices comprises endoluminal devices such as stents, stent-grafts, filters, coils, occlusion baskets, valves, and the like. A stent typically is an elongated device used to support an intraluminal wall. In the case of a stenosis, for example, a stent provides an unobstructed conduit through a body lumen in the area of the stenosis. Such a stent may also have a prosthetic graft layer of fabric or covering lining the inside and/or outside thereof. A covered stent is commonly referred to in the art as an intraluminal prosthesis, an endoluminal or endovascular graft (EVG), a stent-graft, or endograft.

An endograft may be used, for example, to treat a vascular aneurysm by removing or reducing the pressure on a weakened part of an artery so as to reduce the risk of rupture. Typically, an endograft is implanted in a blood vessel at the site of a stenosis or aneurysm endoluminally, i.e. by so-called "minimally invasive techniques" in which the endograft, typically restrained in a radially compressed configuration by a sheath, crocheted or knit web, catheter or other means, is delivered by an endograft delivery system or "introducer" to the site where it is required. The introducer may enter the vessel or lumen from an access location outside the body, such as purcutaneously through the patient's skin, or by a "cut down" technique in which the entry vessel or lumen is exposed by minor surgical means.

U.S. Patent Application Publication No. US 2004/0138734, which is incorporated herein in its entirety by reference, describes systems and methods for the delivery of stents, endovascular grafts, and the like. FIG. 1 herein illustrates a delivery system 10 of such publication for delivering a variety of expandable intracorporeal devices; for example, an expandable endovascular graft 11. One such expandable endovascular graft 11 useful for delivery and deployment at a desired site within a patient is disclosed in U.S. Pat. No. 6,395,019, which is hereby incorporated by reference in its entirety.

Delivery system 10 in FIG. 1 has an elongate shaft 12 with a proximal section 13, a distal section 14, a proximal end 15 and a distal end 16. The distal section 14 has an elongate belt support member in the form of a guidewire tube 17 disposed adjacent a portion of the expandable endovascular graft 11. A guidewire 18 is disposed within guidewire tube 17. A plurality of belts 21, 22, and 23 are secured to the guidewire tube 17 and are circumferentially disposed about portions of the endovascular graft 11. FIG. 1 shows the belts in a configuration that constrains the endovascular graft 11. First and second release members 24 and 25 releasably secure belts 21, 22, and 23 in a constraining configuration as shown.

As defined herein, the proximal end of the elongate shaft is the end 15 proximal to an operator of the delivery system 10 during use. The distal end of the elongate shaft is the end 16 that enters and extends into the patient's body. The proximal and distal directions for the delivery system 10 and endovascular graft 11 loaded within the delivery system 10 as used herein are the same. This convention is used throughout the specification for the purposes of clarity, although other conventions are commonly used.

Belts 21-23 extend circumferentially about the respective portions of the expandable intracorporeal device 11 and are releasably locked together by one or more release members 24 and 25. U.S. Patent Application Publication No. US 2004/0138734 discloses various belt and release wire configurations that may be utilized to secure stents and the like.

To deploy the graft 11, the release wires 24 and 25 are pulled proximally, in a desired sequence, such that the release wires 24 and 25 disengage from the end loops of the belts 21, 22 and 23. It is desired to provide a system and method to minimize the axial force required on the release wires 24 and 25 to release the belts 21, 22 and 23.

SUMMARY OF THE INVENTION

In one aspect, the present invention may provide a securement assembly for releasably securing an expandable endovascular device relative to a delivery tube. The securement assembly comprises a belt base configured for securement relative to the delivery tube. The belt base defines a release member passage and a receiving portion. A first end of a belt is fixed relative to the belt base. The opposite end of the belt includes a retainment portion configured to releasably engage the receiving portion of the belt base. A release member is removably positioned through the release member passage and aligned with the belt retainment portion such that the retainment portion is maintained engaged with the receiving portion until the release member is moved to a non-aligned position.

In accordance with at least one embodiment of the invention, the retainment portion is defined by a member attached to the second end of the belt and the receiving portion is a corresponding slot.

In accordance with at least one embodiment of the invention, the retainment portion is defined by a configuration of the second end of the belt and the receiving portion is a corresponding shoulder.

In accordance with at least one embodiment of the invention, the retainment portion is defined by an opening in the second end of the belt and the receiving portion is defined by a first end of a post extending from the belt base.

In another aspect, the invention may provide a method of releasably securing a portion of an expandable endovascular device relative to a delivery tube. The method comprises securing a belt base relative to the delivery tube, the belt base defining a release member passage and a receiving portion; securing a first end of a belt relative to the belt base; positioning the portion of the expandable endovascular device relative to the belt base; extending the belt about the portion of the expandable endovascular device; releasably engaging a retainment portion of the belt with the receiving portion of the belt base; and removably positioning a release member through the release member passage such that the release member is aligned with the belt retainment portion and maintains such engaged with the receiving portion until the release member is moved to a non-aligned position.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Figure 1:
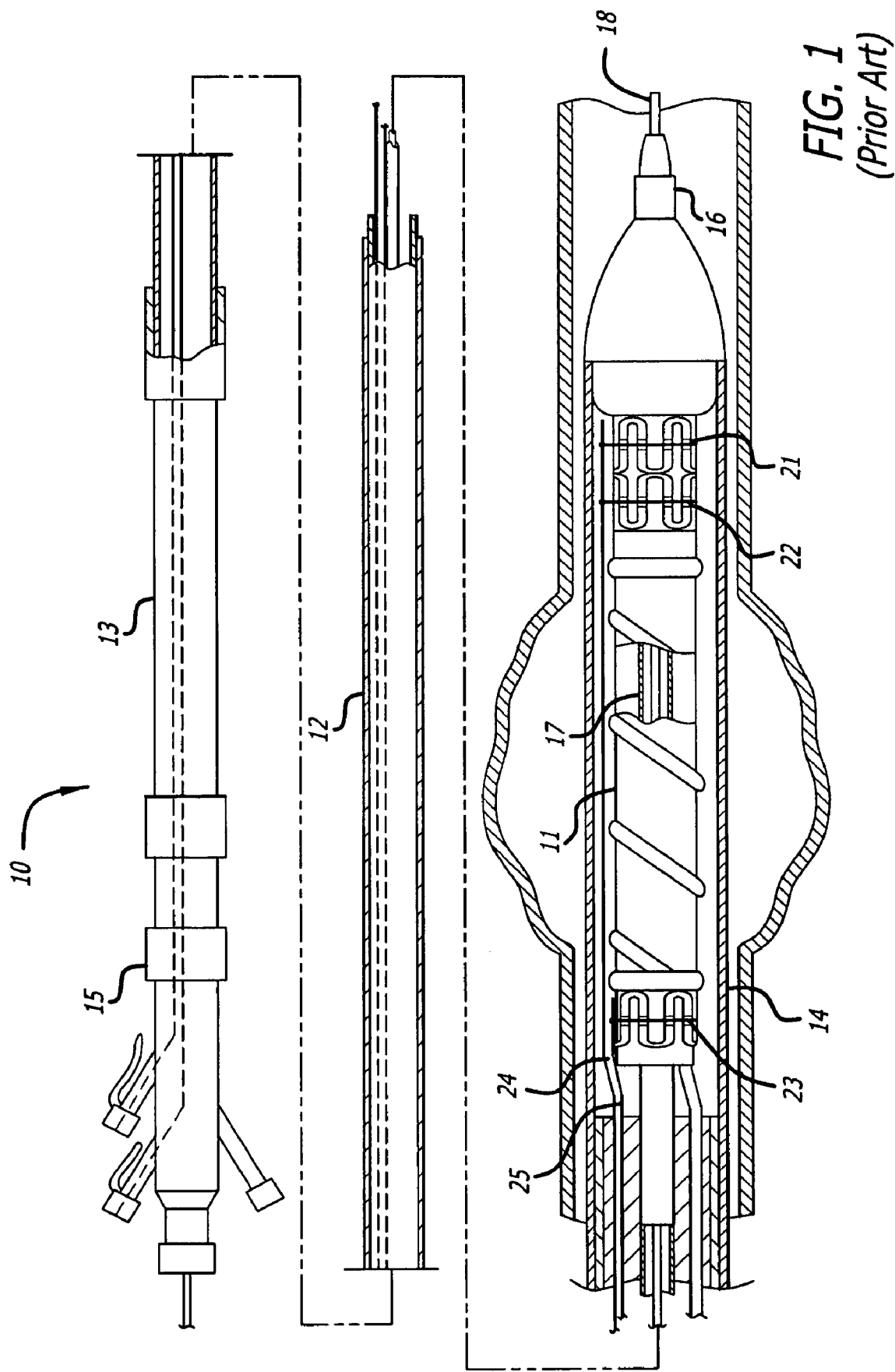
FIG. 1 is a side elevation view in partial section of a prior art endovascular stent graft delivery system.

Referring to FIGS. 2-10, a securement assembly 50 that is a first embodiment of the invention will be described. The securement assembly 50 of the present invention generally comprises a belt base 60, one or more corresponding belts 80 and one or more release wires 52. The securement assemblies are described herein in use with a delivery system as described above with reference to FIG. 1, but may be utilized with other delivery systems for expandable intracorporeal devices. The securement assemblies may be utilized at the proximal or distal end of the delivery system. Furthermore, while each securement assembly described herein is illustrated with a single belt 80 and a single release wire 52, any of the securement assemblies can be configured to support two or more axially spaced belts 80, which may be retained by a common release wire or independent release wires.

Figure 2:
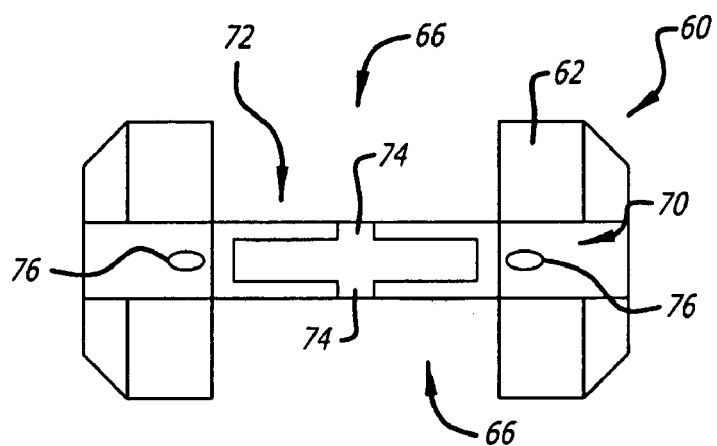
FIG. 2 is a top plan view of a belt base in accordance with a first embodiment of the present invention.
Figure 3:
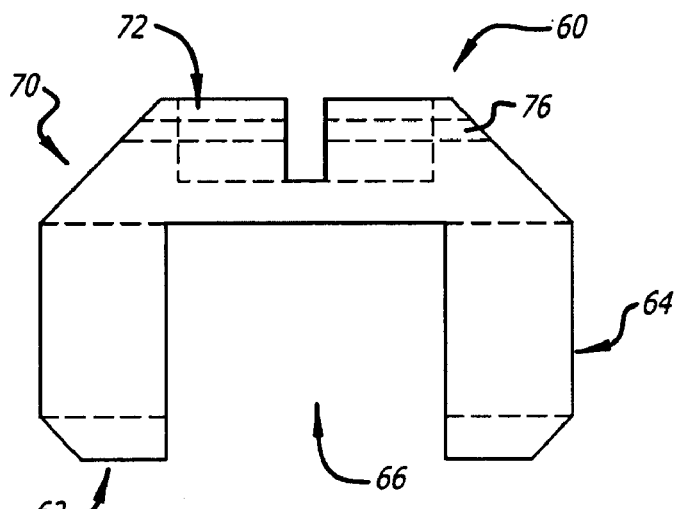
FIG. 3 is a side elevation view of the belt base of FIG. 2.
Figure 4:
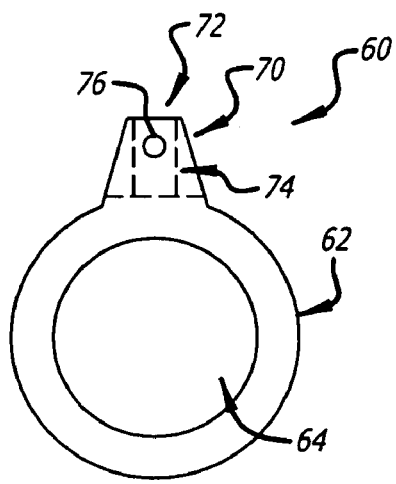
FIG. 4 is an end elevation view of the belt base of FIG. 2.
Figure 5:
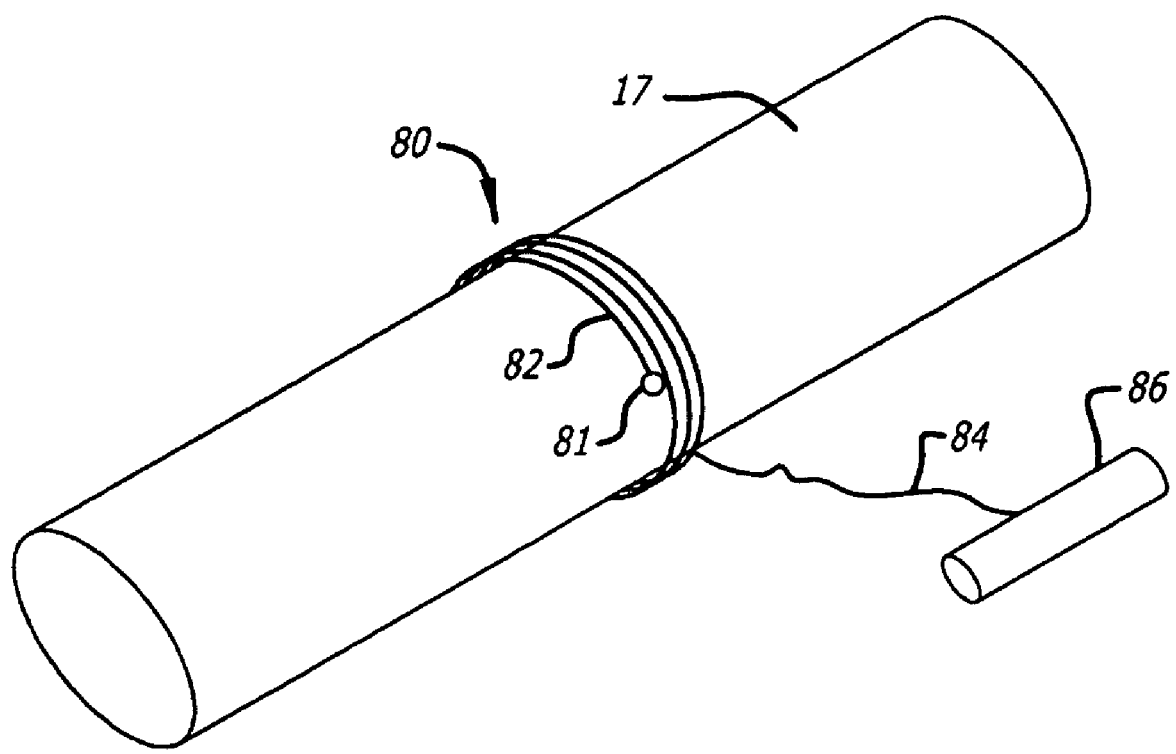
FIG. 5 is a perspective view of a portion of a guidewire tube with a belt in accordance with the first embodiment of the invention attached thereto.
Figure 6:
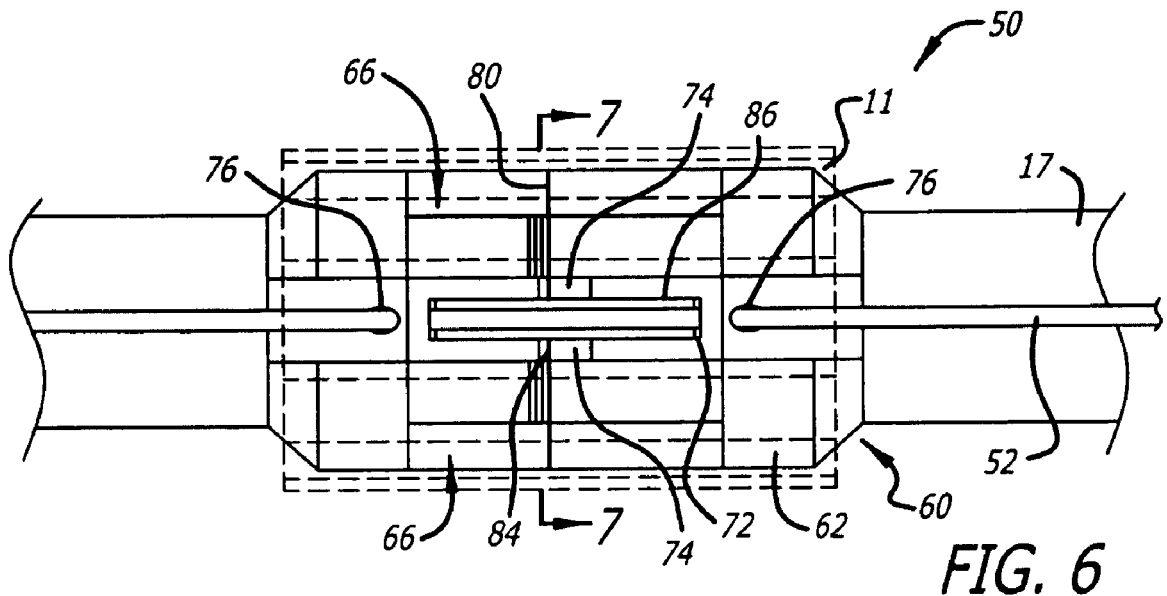
FIG. 6 is a top plan view of the belt base of FIG. 2 positioned about the guidewire tube and the belt secured about an expandable intracorporeal device.
Figure 7:
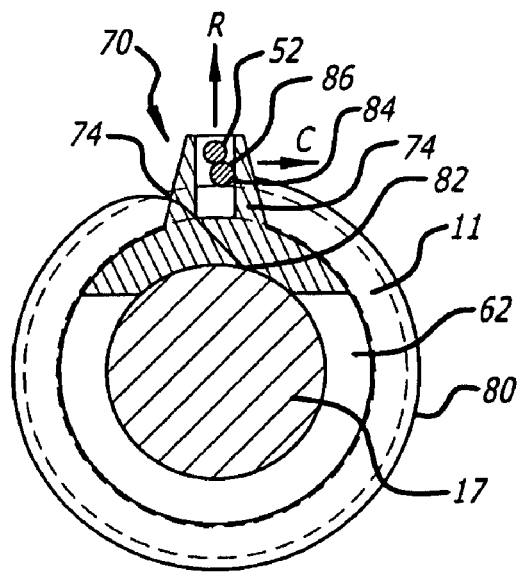
FIG. 7 is a cross-sectional view along the line 7-7 in FIG. 6.

Referring to FIGS. 2-4, a belt base 60 in accordance with the first embodiment of the invention is illustrated. The belt base 60 includes a generally cylindrical body 62 with a passage 64 extending therethrough. The passage 64 is configured to receive the guidewire tube 17 or other support portion of the delivery system, as shown in FIGS. 6 and 7. The inner diameter of the passage 64 is sized to have a close fit over the guidewire tube 17 and secured portion 81, as shown in FIG. 5, of the fixed end 82 of the belt 80 that is secured to the guidewire tube 17. Typically, the inner diameter of the belt base passage 64 ranges from about 0.025 inch to about 0.065 inch; specifically, about 0.030 inch to about 0.050 inch. The belt base 60 may be secured to the guidewire tube 17 with any suitable adhesive such as cyanoacrylate, epoxy or the like. The outer diameter of belt base body 62 is desirably sized to approximate an inner diameter of the respective portion of the expandable endovascular device 11 when such is in a fully constrained state, as shown in phantom in FIGS. 6 and 7. The central portion of the body 62 is open along the sides and bottom as indicated at 66 in FIGS. 2 and 3. The open area 66 allows wrapping of the belt 80 about the expandable device 11 as will be described hereinafter.

A securement portion 70 extends radially from the belt base body 62. The securement portion 70 is configured to radially pass between struts or the like of the expandable endovascular device 11 when such is in a fully constrained state about the belt base 60. The securement portion 70 defines a receiving portion 72 configured to receive a retainment portion 86 at the free end 84 of the belt 80. Referring to FIG. 5, the retainment portion 86 of the present embodiment is a cylindrical rod attached to the free end 84 of the belt 80. The receiving portion 72 has a corresponding configuration. In the present embodiment, the receiving portion 72 has a rectangular configuration such that the retainment portion 86 is receivable therein. The receiving portion 72 is dimensioned such that the retainment portion 86 is easily released therefrom. Lateral openings 74 preferably extend from the receiving portion 72 to the respective open areas 66 to facilitate the belt 80.

A release member passage 76 extends axially through the securement portion 70 circumferentially aligned with the receiving portion 72. The release member passage 76 is configured to receive a release wire 52 or the like, as illustrated in FIGS. 6 and 7. In operation, the expandable endovascular device 11 is positioned about the guidewire tube 17 with a desired portion axially aligned with the belt base 60. For example, a self-expanding stent portion or the like may be aligned with the belt base 60. The free end 84 of the belt 80 is wrapped about the device 11 and tensioned to radially constrain the device 11. As illustrated in FIGS. 6 and 7, the retainment portion 86 of the belt 80 is positioned in the receiving portion 72 and the release wire 52 is positioned through the release member passage 76. The release wire 52 extends above the retainment member 86 in the receiving portion 72 and has a sufficient rigidity to prevent the retainment member 86 from moving radially. As such, the retainment member 86 is retained in the receiving portion 72 and the expandable endovascular device 11 is maintained in a constrained condition until the release wire 52 is removed.

The constrained expandable endovascular device 11 exerts a radial force on the belt 80, however, because the belt 80 extends circumferentially about the expandable endovascular device 11, a large portion of such force is directed circumferentially at the retainment portion 86, as indicated by arrow C in FIG. 7. As such, a significant portion of the constraining force is supported against an inside surface of the receiving portion 72 which is part of the fixed belt base 60. Only a minimal radial force, as indicated by arrow R, is exerted on the retainment portion 86. As such, the force necessary to remove the release wire 52 is a relatively small force to overcome the friction between the release wire 52 and the release member passage 76, which is minimal based on the minimal radial force.

Figure 8:
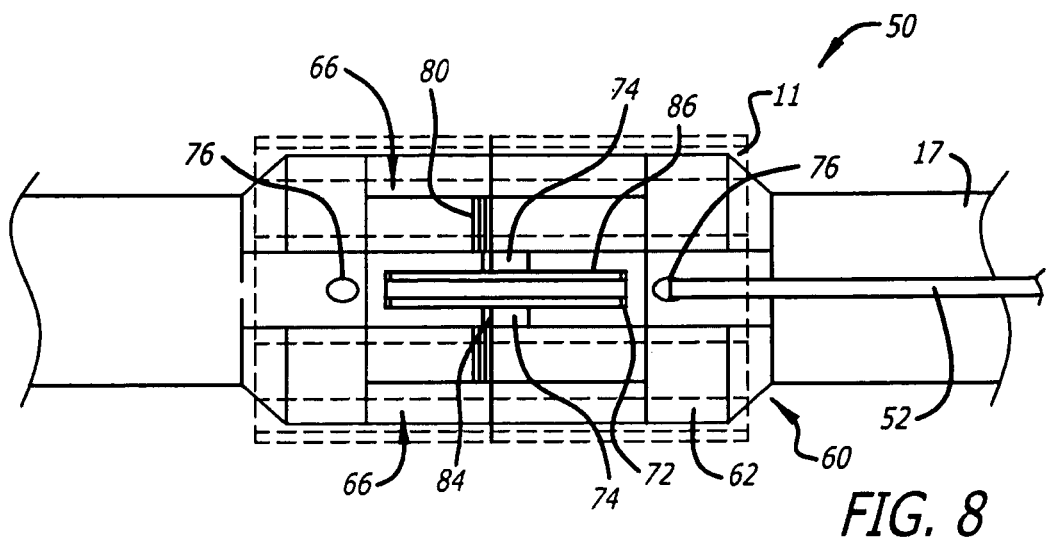
FIG. 8 is a top plan view similar to FIG. 6 and illustrating removal of the release wire.
Figure 9:
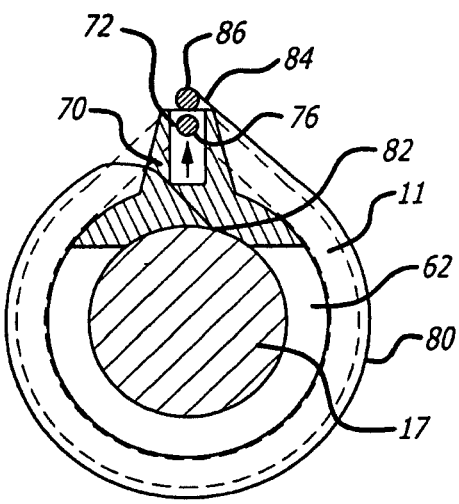
FIGS. 9 and 10 are cross-sectional views similar to FIG. 7 illustrating the progressive release of the belt upon removal of the release wire.
Figure 10:
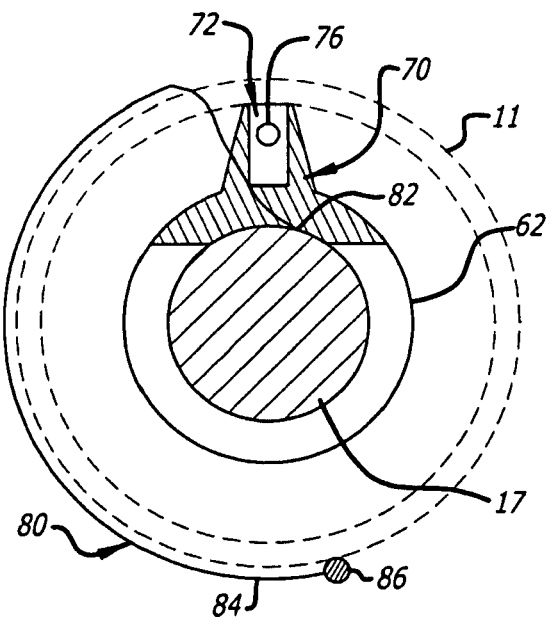

Referring to FIGS. 8-10, upon removal of the release wire 52, the minimal radial force R is sufficient to cause the retainment portion 86 to move radially and release from the receiving portion 72. Once the retainment member 86 is released from the receiving portion 72, the expandable endovascular device 11 is unconstrained and free to expand as illustrated in FIG. 10. After deployment of the expandable endovascular device 11, the guidewire tube 17 is removed with the belt base 60 and belt 80 attached thereto.

Figure 11:
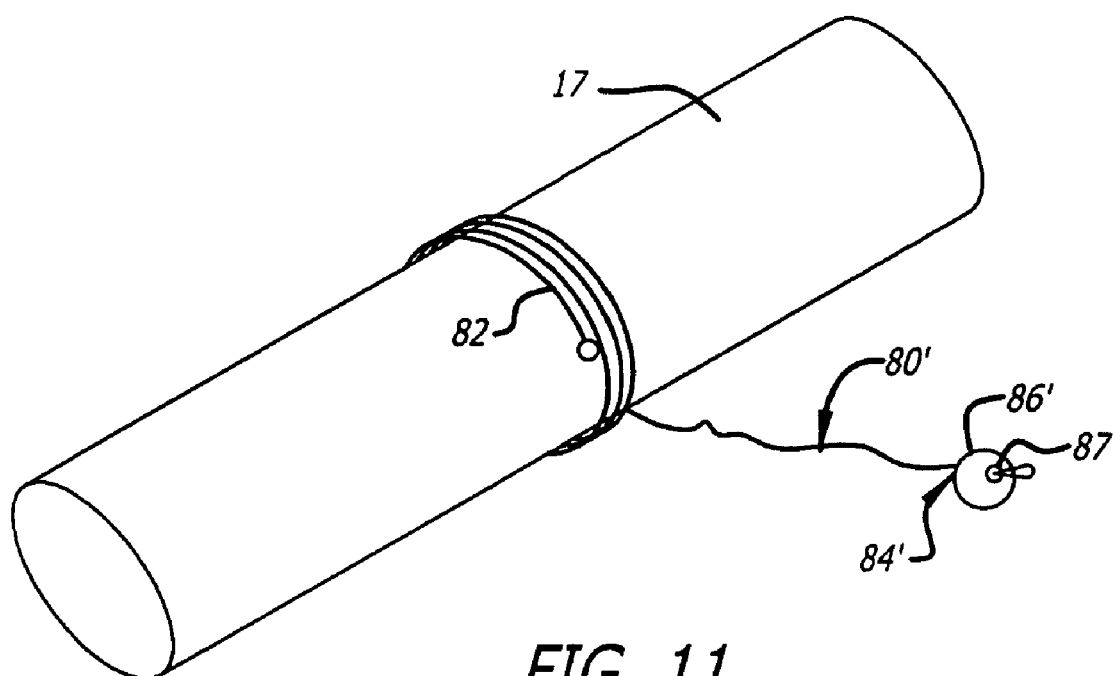
FIG. 11 is a perspective view of a portion of a guidewire tube with a belt in accordance with an alternative embodiment of the invention attached thereto.
Figure 12:
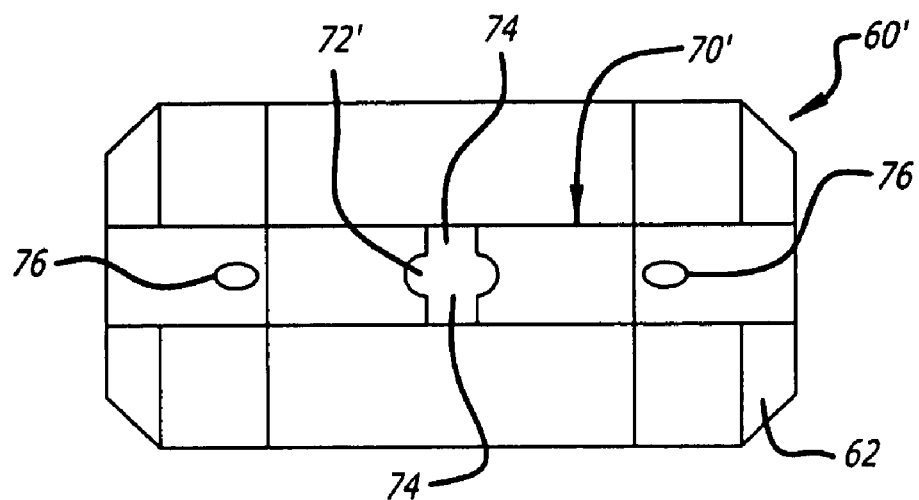
FIG. 12 is a top plan view of a belt base configured for use with the belt illustrated in FIG. 11.

Referring to FIGS. 11 and 12, a securement assembly that is an alternative embodiment of the invention is shown. The securement assembly is substantially the same as in the previous embodiment, except that the retainment portion 86' on the free end 84' of the belt 80' is a sphere rather than a cylindrical rod and the receiving portion 72' on the retainment portion 70' of the belt base 60' has a corresponding semi-spherical configuration. Alternatively, the retainment portion 70' may continue to have a rectangular configuration or may define a shoulder similar to the embodiment described below with respect to FIGS. 16 and 17. As illustrated in FIG. 11, the free end 84' of the belt 80' may be passed through a through hole 87 in the retainment portion 86' and knotted or the like to secure the belt 80' thereto. Other attachment means may alternatively be utilized. Additionally, an adhesive or other sealant (not shown) may be utilized to seal the through hole 87. In all other respects, the securement assembly illustrated in FIGS. 11 and 12 is the same as in the previous embodiment.

Figure 13:
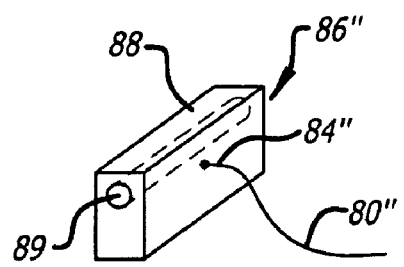
FIG. 13 is a perspective view of an end portion of a belt in accordance with another alternative embodiment of the invention.
Figure 14:
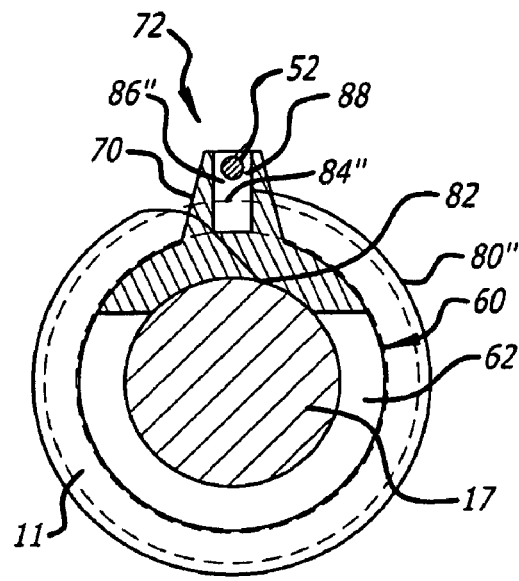
FIG. 14 is a sectional view similar to FIG. 7 illustrating the belt of FIG. 13 secured about an expandable intracorporeal device.

Referring to FIGS. 13 and 14, a securement assembly that is another alternative embodiment of the invention is shown. The securement assembly is substantially the same as in the previous embodiments, except that the retainment portion 86" on the free end 84" of the belt 80" is a block 88 that also includes a release member passage 89. The retainment portion 86" is positioned in the receiving portion 72, having a corresponding shape, and the release wire 52 is inserted through the release member passage 76 in the securement portion 70 of the belt base 60 and through the release member passage 89 extending through the block 88 that defines the retainment portion 86". In all other respects, the securement assembly illustrated in FIGS. 13 and 14 is the same as in the previous embodiments.

Figure 15:
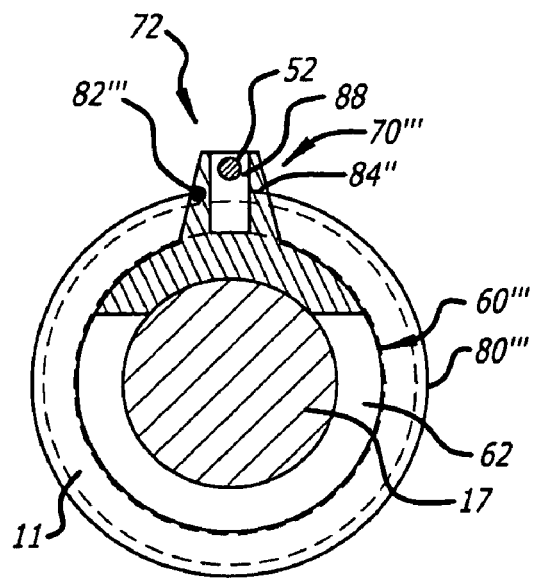
FIG. 15 is a sectional view similar to FIG. 7 illustrating an alternative embodiment of the invention.

Referring to FIG. 15, a securement assembly that is another alternative embodiment of the invention is shown. The securement assembly is substantially the same as in the previous embodiment, except that the fixed end 82''' of the belt 80''' is secured to a portion of the belt base 60''' rather than the guidewire tube 17. In the present embodiment, the fixed end 82''' is secured to the securement portion 70''' of the belt base 60''', but may be otherwise secured. The free end 82''' of the belt 80''' may be secured with any suitable adhesive such as cyanoacrylate, epoxy or the like or otherwise fixed to the belt base 60'''. Securement of the belt free end 82 to the belt base 60 may be utilized in any of the embodiments described herein. In all other respects, the securement assembly illustrated in FIG. 15 is the same as in the previous embodiments.

Figure 16:
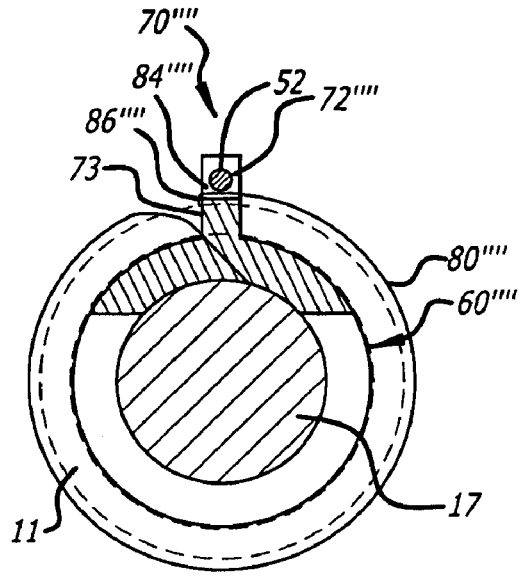
FIG. 16 is a sectional view similar to FIG. 7 illustrating another alternative embodiment of the invention.
Figure 17:
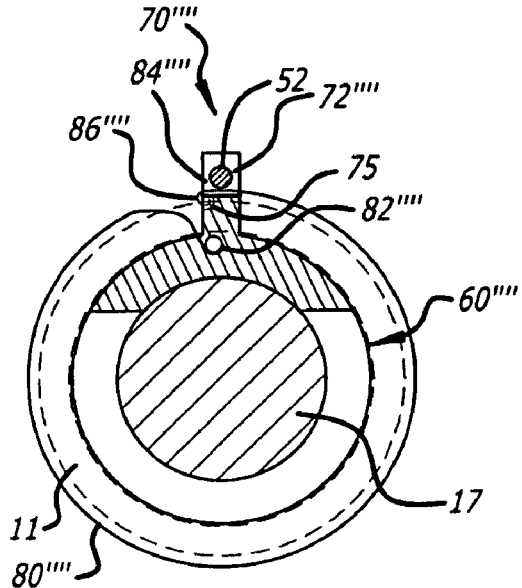
FIG. 17 is a sectional view similar to FIG. 7 illustrating another alternative embodiment of the invention.
Figure 18:
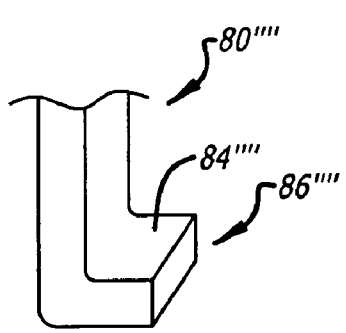
FIGS. 18-20 are perspective views illustrating alternative belt end configurations.
Figure 19:
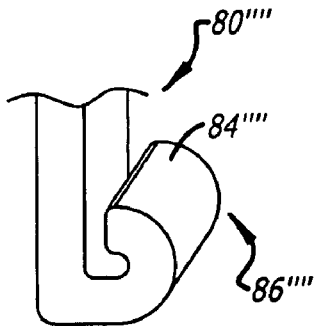
Figure 20:
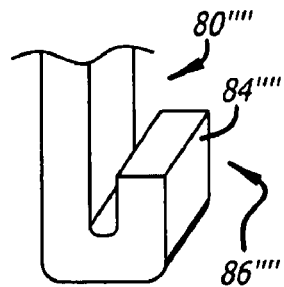

Referring to FIGS. 16-20, additional alternative embodiments of the invention are shown. The securement assembly is substantially the same as in the previous embodiments, except that the retainment portion 86'''' on the free end 84'''' of the belt 80'''' is defined by the configuration of the belt 80'''' rather than a separate component. FIGS. 18-20 illustrate three exemplary configurations of the belt end 84'''' which define the retainment portion 86''''. In FIG. 18, the belt free end 84'''' is formed with a 90° bend to define an L-flange which provides the retainment portion 86''''. As illustrated in FIG. 16, the L-flange engages a shoulder 73 defined on the securement portion 70'''' which provides the receiving portion 72'''' and prevents the belt 80'''' from releasing in the circumferential direction. Similar to the previous embodiments, a release wire 52 extends above the retainment portion 86'''' and prevents radial movement thereof until the release wire 52 is removed. Upon removal of the release wire 52, the expanding endovascular device 11 disengages the L-flange retainment portion 86'''' from the shoulder 73 and the endovascular device 11 is free to fully expand.

In the embodiment illustrated in FIG. 19, the free end 84'''' of the belt 80'''' is wrapped upon itself to define a D-shaped or circular flange which provides the retainment portion 86''''. As illustrated in FIG. 17, the shoulder 73 may include an arcuate recess 75 which provides the receiving portion 72'''' that is configured to receive the D-shaped flange on the belt free end 84''''. Other complimentary configurations of the shoulder 73 are also possible. Also as illustrated in FIG. 17, the fixed end 82'''' of the belt 80'''' may have a configured shape to secure the fixed end 82 relative to the belt base 60''''. In the present embodiment, the fixed end 82'''' has a D-shaped flange configuration which is passed through an opening in the belt base 60'''' and engages an inside surface of the securement portion 70''''. Various end configurations and corresponding belt base configurations may be utilized to secure one or both ends of the belt 80''''. FIG. 20 illustrates another exemplary end configuration wherein the belt end is folded back upon itself to define a U-shaped flange. Other configurations are also possible.

Figure 21:
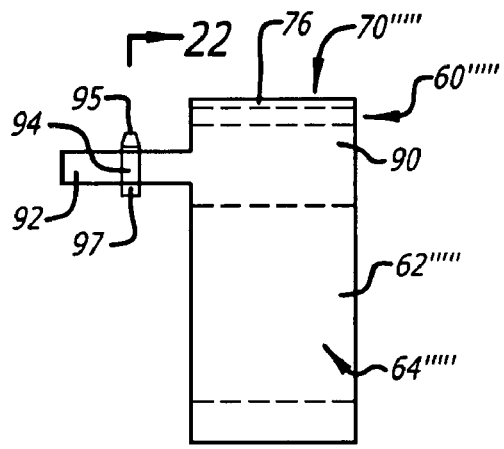
FIG. 21 is a side elevation view of a belt base according to an alternative embodiment of the invention.
Figure 22:
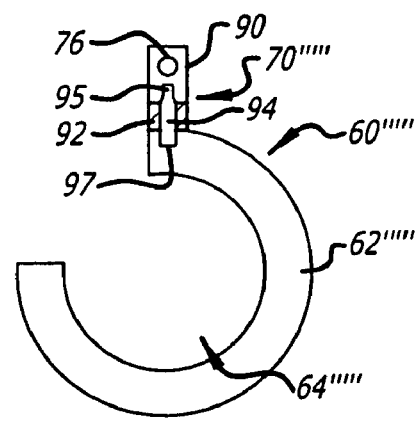
FIG. 22 is a cross-sectional view along the line 22-22 in FIG. 21.

Referring to FIGS. 21-26, another alternative embodiment of the invention is shown. Referring to FIGS. 21 and 22, the belt base 60''''' includes an open cylindrical shaped body 62''''' with a passage 64''''' defined therethrough. Again, the passage 64''''' is configured to receive the guidewire tube 17 or the like and the belt base 60''''' is secured thereto. The open shape of the body 62''''' facilitates greater tolerance and easier assembly of the belt base 60''''' to the guidewire tube 17. Such an open configuration may be utilized in the other embodiments of the invention.

Figure 23:
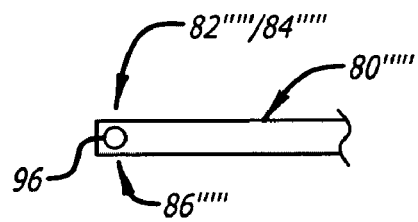
FIGS. 23 and 24 are plan views illustrating alternative belt end configurations.
Figure 24:
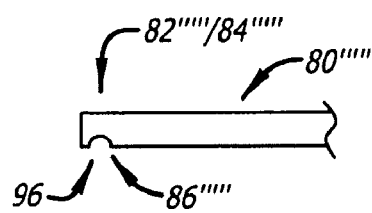

A securement portion 70''''' extends from the body 62''''' and includes a release wire portion 90 and a belt portion 92. The release wire portion 90 defines a release member passage 76. The belt portion 92 extends axially from the release wire portion 90 and supports a belt securement post 94 with each end 95, 97 of the post 94 extending from a respective radial surface of the belt portion 92. Referring to FIGS. 23 and 24, each end 82''''', 84''''' of the belt 80''''' is provided with a post engaging opening 96. The post engaging openings 96 may have various configurations, with a through hole illustrated in FIG. 23 and an arcuate notch illustrated in FIG. 24. Each opening 96 is configured to engage a respective end 95, 97 of the post 94.

Figure 25:
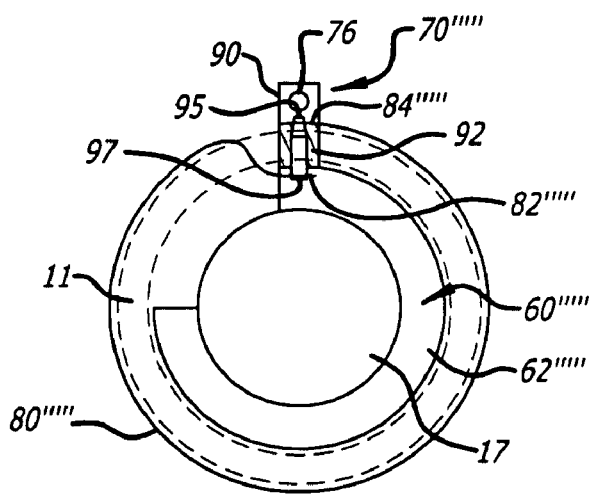
FIG. 25 is a cross-sectional view similar to FIG. 22 illustrating a belt secured about an expandable intracorporeal device.
Figure 26:
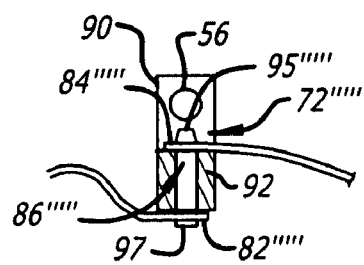
FIG. 26 is an expanded view of the belt interconnection of FIG. 25.

Referring to FIG. 25, in the present embodiment, the fixed end 82''''' of the belt 80''''' is engaged with the radially inner end 97 of the post 94 by positioning the post end 97 into the opening 96. The belt 80''''' is wrapped about the expandable endovascular device 11 and tensioned until the opening 96 at the belt free end 84''''' is engaged with the radially outer end 95 of the post 94 such that the opening 96 defines the retainment portion 86''''' of the belt 80'''''. The end 95 of the post 94 defines the receiving portion 72''''' and prevents the belt 80''''' from releasing in the circumferential direction. Similar to the previous embodiments, a release wire 52 extends through the release member passage 76 above the retainment portion 86'''''' and prevents radial movement thereof until the release wire 52 is removed. Referring to FIG. 26, the radially outer end 95 of the post 94 is desirably tapered to facilitate easier disengagement of the belt engagement portion 86'''''' upon removal of the release wire 52. Furthermore, the post 94 may be provided with a slight radial clearance such that upon tensioning and securement of the belt 80'''''' with the post 94, the post 94 tilts based on the tension. As such, the end 95 tilts toward the removal direction, thereby further facilitating easier disengagement of the belt engagement portion 86'''''' upon removal of the release wire 52.

The belts 80, 80', 80'', 80''', 80'''' and 80'''''' can have various cross-sectional shapes including, but not limited to, round, square and rectangular. Additionally, the belts 80, 80', 80'', 80''', 80'''' and 80'''''' may be made from various ferrous and non-ferrous materials including nickel titanium and other metallic alloys such as stainless steel or high strength fibers such as carbon, Kevlar®, polytetrafluoroethylene (PTFE), polyimide, or the like.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A securement assembly for releasably securing an expandable stent or stent-graft relative to a delivery tube for delivery to a position within a patient's body lumen, the securement assembly comprising:

a belt base configured for securement relative to the delivery tube, the belt base defining a release member passage and a receiving portion;

a belt including a first end and a second end, the first end fixed relative to the belt base, the second end including a retainment portion configured to releasably engage the receiving portion of the belt base; and a release member removably positioned through the release member passage and aligned with the belt retainment portion such that the retainment portion is maintained engaged with the receiving portion until the release member is moved to a non-aligned position.

2. The securement assembly of claim 1 wherein the retainment portion is defined by a member attached to the second end of the belt and the receiving portion is a corresponding slot.

3. The securement assembly of claim 2 wherein the release member passage is circumferentially aligned with the slot.

4. The securement assembly of claim 2 wherein the release member is a cylindrical rod and the slot is a rectangular slot.

5. The securement assembly of claim 1 wherein the first end of the belt is fixed directly to the belt base.

6. The securement assembly of claim 1 further comprising a delivery tube wherein the first end of the belt is fixed to the delivery tube.

7. The securement assembly of claim 1 wherein the first end of the belt has a shaped configuration which engages a portion of the belt base and fixes the first end relative thereto.

8. The securement assembly of claim 1 wherein the retainment portion is defined by a configuration of the second end of the belt and the receiving portion is a corresponding shoulder.

\* \* \* \* \*